(12) United States Patent
Kochenderfer

(10) Patent No.: US 10,815,301 B2
(45) Date of Patent: Oct. 27, 2020

(54) ANTI-CD30 CHIMERIC ANTIGEN RECEPTORS

(71) Applicant: The United States of America, as represented by the Secretary, Department of Health and Human Services, Bethesda, MD (US)

(72) Inventor: James N. Kochenderfer, Bethesda, MD (US)

(73) Assignee: The United States of America, as represented by the Secretary, Department of Health and Human Service, Bethesda, MD (US)

( * ) Notice: Subject to any disclaimer, the term of this patent is extended or adjusted under 35 U.S.C. 154(b) by 267 days.

(21) Appl. No.: 15/766,948

(22) PCT Filed: Oct. 10, 2016

(86) PCT No.: PCT/US2016/056262
§ 371 (c)(1),
(2) Date: Apr. 9, 2018

(87) PCT Pub. No.: WO2017/066122
PCT Pub. Date: Apr. 20, 2017

(65) Prior Publication Data
US 2019/0062426 A1 Feb. 28, 2019

Related U.S. Application Data

(60) Provisional application No. 62/241,896, filed on Oct. 15, 2015.

(51) Int. Cl.
*C07K 16/28* (2006.01)
*A61P 35/00* (2006.01)
*C07K 14/705* (2006.01)
*A61K 39/00* (2006.01)

(52) U.S. Cl.
CPC .......... *C07K 16/2803* (2013.01); *A61P 35/00* (2018.01); *C07K 14/70517* (2013.01); *C07K 14/70521* (2013.01); *C07K 16/2878* (2013.01); *A61K 2039/505* (2013.01); *C07K 2317/53* (2013.01); *C07K 2317/622* (2013.01); *C07K 2317/73* (2013.01); *C07K 2319/03* (2013.01)

(58) Field of Classification Search
None
See application file for complete search history.

(56) References Cited

U.S. PATENT DOCUMENTS

| | | |
|---|---|---|
| 7,387,776 B2 | 6/2008 | Keler et al. |
| 8,034,334 B2 | 10/2011 | Dudley et al. |
| 8,383,099 B2 | 2/2013 | Dudley et al. |
| 2005/0123536 A1 | 6/2005 | Law et al. |
| 2012/0014943 A1 | 1/2012 | Lazar et al. |
| 2012/0213783 A1* | 8/2012 | Rosenberg ......... C07K 14/7051 424/134.1 |
| 2012/0244133 A1 | 9/2012 | Rosenberg et al. |
| 2018/0142034 A1* | 5/2018 | Chang .............. C07K 14/70521 |

FOREIGN PATENT DOCUMENTS

| | | | |
|---|---|---|---|
| WO | WO-2014055771 A1 * | 4/2014 | ......... C07K 14/7051 |
| WO | WO 2015/028444 A1 | 3/2015 | |
| WO | WO 2016/116035 A1 | 7/2016 | |
| WO | WO 2016/134284 A1 | 8/2016 | |

OTHER PUBLICATIONS

Jena et al. (Blood Aug. 19, 2010 116(7): 1035-1044) (Year: 2010).*
Bonini and Mondino (Eur. J. Innnnunol. 2015 45: 2457-2469) (Year: 2015).*
Carpenter et al., "B-cell Maturation Antigen is a Promising Target for Adoptive T-cell Therapy of Multiple Myeloma," *Clin. Cancer Res.*, 19(8): 2048-2060 (2013).
Clinical Trial NCT02274584 "CAR T Cells Targeting CD30 Positive Lymphomas (4SCAR30273)," accessed online at <//clinicaltrials.gov/ct2/show/record/NCT02274584> printed Oct. 8, 2015.
Database Accession No. ATS30832 "Bispecific single chain antibody protein sequence, SEQ: 1123" (2008).
Database Accession No. BBZ09420 "GMCSFRss-R11scFv-Hinge-CH2-CH3-CD28tm/41BB-Z-T2A-tEGFR construct SEQ 54" (2015).
Database Accession No. BCA49146 "Human CD4-35-17b CAR fusion protein, SEQ ID 5" (2015).
Di Stasi et al., "T lymphocytes coexpressing CCR4 and a chimeric antigen receptor targeting CD30 have improved homing and antitumor activity in a Hodgkin tumor model," *Blood*, 113(25): 6392-6402 (2009).
Dudley et al., "Generation of Tumor-Infiltrating Lymphocyte Cultures for Use in Adoptive Transfer Therapy for Melanoma Patients," *J. Immunother.*, 26(4): 332-342 (2003).
Engert et al., "Antitumor Effects of Ricin A Chain Immunotoxins Prepared from Intact Antibodies and Fab' Fragments on Solid Human Hodgkin's Disease Tumors in Mice," *Cancer Res.*, 50: 2929-2935 (1990).
Eshhar et al., "Specific activation and targeting of cytotoxic lymphocytes through chimeric single chains consisting of antibody-binding domains and the γ or ζ subunits of the immunoglobulin and T-cell receptors," *PNAS*, 90(2): 720-724 (1993).
Falini et al., "CD30 (Ki-1) molecule: a new cytokine receptor of the tumor necrosis factor receptor superfamily as a tool for diagnosis and immunotherapy," *Blood*, 85(1): 1-14 (1995).
Hombach et al., "An Anti-CD30 Chimeric Receptor That Mediates CD3-ζ-independent T-Cell Activation against Hodgkin's Lymphoma Cells in the Presence of Soluble CD30," *Cancer Res.*, 58(6): 1116-1119 (1998).

(Continued)

*Primary Examiner* — Peter J Reedig
(74) *Attorney, Agent, or Firm* — Leydig, Voit & Mayer

(57) ABSTRACT

Chimeric antigen receptors (CARs) that specifically bind to and immunologically recognize CD30 are disclosed. Related nucleic acids, recombinant expression vectors, host cells, populations of cells, and pharmaceutical compositions relating to the CARs are also disclosed. Methods of treating or preventing a condition in a mammal, wherein the condition is cancer, are also disclosed.

21 Claims, 8 Drawing Sheets
Specification includes a Sequence Listing.

(56) References Cited

OTHER PUBLICATIONS

Hombach et al., "Characterization of a Chimeric T-Cell Receptor with Specificity for the Hodgkin's Lymphoma-Associated CD30 Antigen," *J. Immunother.*, 22(6): 473-480 (1999).
Horie et al., "CD30: expression and function in health and disease," *Seminars in Immunology*, 10(6): 457-470 (1998).
Hughes et al., "Transfer of a TCR Gene Derived from a Patient with a Marked Antitumor Response Conveys Highly Active T-Cell Effector Functions," *Human Gene Ther.*, 16(4): 457-472 (2005).
International Bureau, International Search Report and Written Opinion in International Application No. PCT/US2016/056262, dated Jan. 16, 2017.
Ito et al., "High expression of the CD30 molecule in human decidual cells," *American J. Pathol.*, 145(2): 276-280 (1994).
Kochenderfer et al, "Construction and Pre-clinical Evaluation of an Anti-CD19 Chimeric Antigen Receptor," *J. Immunother*, 32(7): 689-702 (2009).
Mannering et al., "A sensitive method for detecting proliferation of rare autoantigen-specific human T cells," *J. Immunol. Methods*, 283(1-2): 173-183 (2003).
Nagata et al., "Cell membrane-specific epitopes on CD30: Potentially superior targets for immunotherapy," *PNAS*, 102(22): 7946-7951 (2005).
Pizzolo et al., "Serum levels of soluble CD30 molecule (Ki-1 antigen) in Hodgkin's disease: relationship with disease activity and clinical stage," *British J. Haematol.*, 75(2): 282-284 (1990).
Ramos et al., "CAR-T Cell Therapy for Lymphoma," *Ann. Rev. Med.*, 67(1): 165-183 (Aug. 26, 2015).
Ramos et al., "Chimeric T Cells for Therapy of CD30+ Hodgkin and Non-Hodgkin Lymphomas," *Blood*, 126(23) American Society of Hematology (ASH) abstracts, Dec. 3, 2015.
Ramos et al., "RAC 1004-1034 Protocol: Phase I Study of the Administration of EBV CTLs Expressing CD30 Chimeric Receptors (CAR.CD30) for Relapsed CD30+ Hodgkin Lymphoma and CD30+ Non-Hodgkin Lymphoma," accessed online at <//osp.od.nih.gov/wp-content/uploads/2013/12/2_P1034_Heslop_cln.pdf> on Oct. 8, 2015.
Riddell et al., "The use of anti-CD3 and anti-CD28 monoclonal antibodies to clone and expand human antigen-specific T cells," *J. Immunol. Methods*, 128: 189-201 (1990).
Savoldo et al., "Epstein Barr virus-specific cytotoxic T lymphocytes expressing the anti-CD30ζ artificial chimeric T-cell receptor for immunotherapy of Hodgkin disease," *Blood*, 110(7): 2620-2630 (2007).
Schwarting et al., "BER-H2: a new anti-Ki-1 (CD30) monoclonal antibody directed at a formol-resistant epitope," *Blood*, 74(5): 1678-1689 (1989).
Stein et al., "The expression of the Hodgkin's disease associated antigen Ki-1 in reactive and neoplastic lymphoid tissue: evidence that Reed-Sternberg cells and histiocytic malignancies are derived from activated lymphoid cells," *Blood*, 66(4): 848-858 (1985).
Visco et al., "Very high levels of soluble CD30 recognize the patients with classical Hodgkin's lymphoma retaining a very poor prognosis," *European J. Haematol.*, 77(5): 387-394 (2006).
Yang et al., "A simplified method for the clinical-scale generation of central memory-like CD8+ T cells after transduction with lentiviral vectors encoding antitumor antigen T-cell receptors," *J. Immunother.*, 33(6): 648-658 (2010).
Ying et al., "First-in-Patient Proof of Safety and Efficacy of a $4^{th}$ Generation Chimeric Antigen Receptor-Modified T cells for the Treatment of Relapsed or Refractory CD30 Positive Lymphomas," abstract of poster session at the American Society of Gene & Cell Therapy annual meeting, May 14, 2015.

* cited by examiner

A. 5F11-28Z

B. 5F11-CD828Z

C. 5F11-CD8BBZ

A

B

SEQUENCE LISTING

```
<160> NUMBER OF SEQ ID NOS: 23

<210> SEQ ID NO 1
<211> LENGTH: 5
<212> TYPE: PRT
<213> ORGANISM: Homo sapiens

<400> SEQUENCE: 1

Ala Tyr Tyr Trp Ser
1               5
```

```
<210> SEQ ID NO 2
<211> LENGTH: 16
<212> TYPE: PRT
<213> ORGANISM: Homo sapiens

<400> SEQUENCE: 2

Asp Ile Asn His Gly Gly Gly Thr Asn Tyr Asn Pro Ser Leu Lys Ser
1               5                   10                  15

<210> SEQ ID NO 3
<211> LENGTH: 4
<212> TYPE: PRT
<213> ORGANISM: Homo sapiens

<400> SEQUENCE: 3

Leu Thr Ala Tyr
1

<210> SEQ ID NO 4
<211> LENGTH: 11
<212> TYPE: PRT
<213> ORGANISM: Homo sapiens

<400> SEQUENCE: 4

Arg Ala Ser Gln Gly Ile Ser Ser Trp Leu Thr
1               5                   10

<210> SEQ ID NO 5
<211> LENGTH: 7
<212> TYPE: PRT
<213> ORGANISM: Homo sapiens

<400> SEQUENCE: 5

Ala Ala Ser Ser Leu Gln Ser
1               5

<210> SEQ ID NO 6
<211> LENGTH: 9
<212> TYPE: PRT
<213> ORGANISM: Homo sapiens

<400> SEQUENCE: 6

Gln Gln Tyr Asp Ser Tyr Pro Ile Thr
1               5

<210> SEQ ID NO 7
<211> LENGTH: 112
<212> TYPE: PRT
<213> ORGANISM: Homo sapiens

<400> SEQUENCE: 7

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Ala Tyr
            20                  25                  30

Tyr Trp Ser Trp Ile Arg Gln Pro Pro Gly Lys Gly Leu Glu Trp Ile
        35                  40                  45

Gly Asp Ile Asn His Gly Gly Gly Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Asn Ser Val Thr Ala Ala Asp Thr Ala Val Tyr Tyr Cys Ala
```

```
                    85                  90                  95

Ser Leu Thr Ala Tyr Trp Gly Gln Gly Ser Leu Val Thr Val Ser Ser
                100                 105                 110

<210> SEQ ID NO 8
<211> LENGTH: 107
<212> TYPE: PRT
<213> ORGANISM: Homo sapiens

<400> SEQUENCE: 8

Asp Ile Gln Met Thr Gln Ser Pro Thr Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Thr Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Ser Tyr Pro Ile
                85                  90                  95

Thr Phe Gly Gln Gly Thr Arg Leu Glu Ile Lys
            100                 105

<210> SEQ ID NO 9
<211> LENGTH: 21
<212> TYPE: PRT
<213> ORGANISM: Homo sapiens

<400> SEQUENCE: 9

Met Ala Leu Pro Val Thr Ala Leu Leu Leu Pro Leu Ala Leu Leu Leu
1               5                   10                  15

His Ala Ala Arg Pro
            20

<210> SEQ ID NO 10
<211> LENGTH: 18
<212> TYPE: PRT
<213> ORGANISM: Artificial Sequence
<220> FEATURE:
<223> OTHER INFORMATION: Synthetic

<400> SEQUENCE: 10

Gly Ser Thr Ser Gly Ser Gly Lys Pro Gly Ser Gly Glu Gly Ser Thr
1               5                   10                  15

Lys Gly

<210> SEQ ID NO 11
<211> LENGTH: 83
<212> TYPE: PRT
<213> ORGANISM: Homo sapiens

<400> SEQUENCE: 11

Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
            20                  25                  30

Arg Pro Glu Ala Cys Arg Pro Ala Ala Gly Gly Ala Val His Thr Arg
        35                  40                  45
```

Gly Leu Asp Phe Ala Cys Asp Ile Tyr Ile Trp Ala Pro Leu Ala Gly
        50                  55                  60

Thr Cys Gly Val Leu Leu Ser Leu Val Ile Thr Leu Tyr Cys Asn
 65                  70                  75                  80

His Arg Asn

<210> SEQ ID NO 12
<211> LENGTH: 41
<212> TYPE: PRT
<213> ORGANISM: Homo sapiens

<400> SEQUENCE: 12

Arg Ser Lys Arg Ser Arg Leu Leu His Ser Asp Tyr Met Asn Met Thr
 1               5                  10                  15

Pro Arg Arg Pro Gly Pro Thr Arg Lys His Tyr Gln Pro Tyr Ala Pro
             20                  25                  30

Pro Arg Asp Phe Ala Ala Tyr Arg Ser
         35                  40

<210> SEQ ID NO 13
<211> LENGTH: 107
<212> TYPE: PRT
<213> ORGANISM: Homo sapiens

<400> SEQUENCE: 13

Ile Glu Val Met Tyr Pro Pro Pro Tyr Leu Asp Asn Glu Lys Ser Asn
 1               5                  10                  15

Gly Thr Ile Ile His Val Lys Gly Lys His Leu Cys Pro Ser Pro Leu
             20                  25                  30

Phe Pro Gly Pro Ser Lys Pro Phe Trp Val Leu Val Val Val Gly Gly
         35                  40                  45

Val Leu Ala Cys Tyr Ser Leu Leu Val Thr Val Ala Phe Ile Ile Phe
     50                  55                  60

Trp Val Arg Ser Lys Arg Ser Arg Leu Leu His Ser Asp Tyr Met Asn
 65                  70                  75                  80

Met Thr Pro Arg Arg Pro Gly Pro Thr Arg Lys His Tyr Gln Pro Tyr
                 85                  90                  95

Ala Pro Pro Arg Asp Phe Ala Ala Tyr Arg Ser
             100                 105

<210> SEQ ID NO 14
<211> LENGTH: 42
<212> TYPE: PRT
<213> ORGANISM: Homo sapiens

<400> SEQUENCE: 14

Lys Arg Gly Arg Lys Lys Leu Leu Tyr Ile Phe Lys Gln Pro Phe Met
 1               5                  10                  15

Arg Pro Val Gln Thr Thr Gln Glu Glu Asp Gly Cys Ser Cys Arg Phe
             20                  25                  30

Pro Glu Glu Glu Glu Gly Gly Cys Glu Leu
         35                  40

<210> SEQ ID NO 15
<211> LENGTH: 112
<212> TYPE: PRT
<213> ORGANISM: Homo sapiens

<400> SEQUENCE: 15

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
                35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
                100                 105                 110
```

<210> SEQ ID NO 16
<211> LENGTH: 456
<212> TYPE: PRT
<213> ORGANISM: Artificial Sequence
<220> FEATURE:
<223> OTHER INFORMATION: Synthetic

<400> SEQUENCE: 16

```
Asp Ile Gln Met Thr Gln Ser Pro Thr Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Thr Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Ser Tyr Pro Ile
                85                  90                  95

Thr Phe Gly Gln Gly Thr Arg Leu Glu Ile Lys Gly Ser Thr Ser Gly
                100                 105                 110

Ser Gly Lys Pro Gly Ser Gly Glu Gly Ser Thr Lys Gly Gln Val Gln
            115                 120                 125

Leu Gln Gln Trp Gly Ala Gly Leu Leu Lys Pro Ser Glu Thr Leu Ser
        130                 135                 140

Leu Thr Cys Ala Val Tyr Gly Gly Ser Phe Ser Ala Tyr Tyr Trp Ser
145                 150                 155                 160

Trp Ile Arg Gln Pro Pro Gly Lys Gly Leu Glu Trp Ile Gly Asp Ile
                165                 170                 175

Asn His Gly Gly Gly Thr Asn Tyr Asn Pro Ser Leu Lys Ser Arg Val
            180                 185                 190

Thr Ile Ser Val Asp Thr Ser Lys Asn Gln Phe Ser Leu Lys Leu Asn
        195                 200                 205

Ser Val Thr Ala Ala Asp Thr Ala Val Tyr Tyr Cys Ala Ser Leu Thr
    210                 215                 220

Ala Tyr Trp Gly Gln Gly Ser Leu Val Thr Val Ser Ser Ile Glu Val
225                 230                 235                 240

Met Tyr Pro Pro Pro Tyr Leu Asp Asn Glu Lys Ser Asn Gly Thr Ile
                245                 250                 255
```

```
Ile His Val Lys Gly Lys His Leu Cys Pro Ser Pro Leu Phe Pro Gly
            260                 265                 270

Pro Ser Lys Pro Phe Trp Val Leu Val Val Gly Val Leu Ala
        275                 280                 285

Cys Tyr Ser Leu Leu Val Thr Val Ala Phe Ile Ile Phe Trp Val Arg
290                 295                 300

Ser Lys Arg Ser Arg Leu Leu His Ser Asp Tyr Met Asn Met Thr Pro
305                 310                 315                 320

Arg Arg Pro Gly Pro Thr Arg Lys His Tyr Gln Pro Tyr Ala Pro Pro
                325                 330                 335

Arg Asp Phe Ala Ala Tyr Arg Ser Arg Val Lys Phe Ser Arg Ser Ala
            340                 345                 350

Asp Ala Pro Ala Tyr Gln Gln Gly Gln Asn Gln Leu Tyr Asn Glu Leu
        355                 360                 365

Asn Leu Gly Arg Arg Glu Glu Tyr Asp Val Leu Asp Lys Arg Arg Gly
    370                 375                 380

Arg Asp Pro Glu Met Gly Gly Lys Pro Arg Arg Lys Asn Pro Gln Glu
385                 390                 395                 400

Gly Leu Tyr Asn Glu Leu Gln Lys Asp Lys Met Ala Glu Ala Tyr Ser
                405                 410                 415

Glu Ile Gly Met Lys Gly Glu Arg Arg Arg Gly Lys Gly His Asp Gly
            420                 425                 430

Leu Tyr Gln Gly Leu Ser Thr Ala Thr Lys Asp Thr Tyr Asp Ala Leu
        435                 440                 445

His Met Gln Ala Leu Pro Pro Arg
    450                 455

<210> SEQ ID NO 17
<211> LENGTH: 473
<212> TYPE: PRT
<213> ORGANISM: Artificial Sequence
<220> FEATURE:
<223> OTHER INFORMATION: Synthetic

<400> SEQUENCE: 17

Asp Ile Gln Met Thr Gln Ser Pro Thr Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Thr Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Ser Tyr Pro Ile
                85                  90                  95

Thr Phe Gly Gln Gly Thr Arg Leu Glu Ile Lys Gly Ser Thr Ser Gly
            100                 105                 110

Ser Gly Lys Pro Gly Ser Gly Glu Gly Ser Thr Lys Gly Gln Val Gln
        115                 120                 125

Leu Gln Gln Trp Gly Ala Gly Leu Leu Lys Pro Ser Glu Thr Leu Ser
    130                 135                 140

Leu Thr Cys Ala Val Tyr Gly Gly Ser Phe Ser Ala Tyr Tyr Trp Ser
145                 150                 155                 160
```

```
Trp Ile Arg Gln Pro Pro Gly Lys Gly Leu Glu Trp Ile Gly Asp Ile
                165                 170                 175
Asn His Gly Gly Gly Thr Asn Tyr Asn Pro Ser Leu Lys Ser Arg Val
            180                 185                 190
Thr Ile Ser Val Asp Thr Ser Lys Asn Gln Phe Ser Leu Lys Leu Asn
        195                 200                 205
Ser Val Thr Ala Ala Asp Thr Ala Val Tyr Tyr Cys Ala Ser Leu Thr
    210                 215                 220
Ala Tyr Trp Gly Gln Gly Ser Leu Val Thr Val Ser Ser Phe Val Pro
225                 230                 235                 240
Val Phe Leu Pro Ala Lys Pro Thr Thr Thr Pro Ala Pro Arg Pro Pro
                245                 250                 255
Thr Pro Ala Pro Thr Ile Ala Ser Gln Pro Leu Ser Leu Arg Pro Glu
            260                 265                 270
Ala Cys Arg Pro Ala Ala Gly Gly Ala Val His Thr Arg Gly Leu Asp
        275                 280                 285
Phe Ala Cys Asp Ile Tyr Ile Trp Ala Pro Leu Ala Gly Thr Cys Gly
    290                 295                 300
Val Leu Leu Leu Ser Leu Val Ile Thr Leu Tyr Cys Asn His Arg Asn
305                 310                 315                 320
Arg Ser Lys Arg Ser Arg Leu Leu His Ser Asp Tyr Met Asn Met Thr
                325                 330                 335
Pro Arg Arg Pro Gly Pro Thr Arg Lys His Tyr Gln Pro Tyr Ala Pro
            340                 345                 350
Pro Arg Asp Phe Ala Ala Tyr Arg Ser Arg Val Lys Phe Ser Arg Ser
        355                 360                 365
Ala Asp Ala Pro Ala Tyr Gln Gln Gly Gln Asn Gln Leu Tyr Asn Glu
    370                 375                 380
Leu Asn Leu Gly Arg Arg Glu Glu Tyr Asp Val Leu Asp Lys Arg Arg
385                 390                 395                 400
Gly Arg Asp Pro Glu Met Gly Gly Lys Pro Arg Arg Lys Asn Pro Gln
                405                 410                 415
Glu Gly Leu Tyr Asn Glu Leu Gln Lys Asp Lys Met Ala Glu Ala Tyr
            420                 425                 430
Ser Glu Ile Gly Met Lys Gly Glu Arg Arg Arg Gly Lys Gly His Asp
        435                 440                 445
Gly Leu Tyr Gln Gly Leu Ser Thr Ala Thr Lys Asp Thr Tyr Asp Ala
    450                 455                 460
Leu His Met Gln Ala Leu Pro Pro Arg
465                 470

<210> SEQ ID NO 18
<211> LENGTH: 474
<212> TYPE: PRT
<213> ORGANISM: Artificial Sequence
<220> FEATURE:
<223> OTHER INFORMATION: Synthetic

<400> SEQUENCE: 18

Asp Ile Gln Met Thr Gln Ser Pro Thr Ser Leu Ser Ala Ser Val Gly
1               5                   10                  15
Asp Arg Val Thr Ile Thr Cys Arg Ala Ser Gln Gly Ile Ser Ser Trp
            20                  25                  30
Leu Thr Trp Tyr Gln Gln Lys Pro Glu Lys Ala Pro Lys Ser Leu Ile
        35                  40                  45
```

```
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Asp Ser Tyr Pro Ile
                85                  90                  95
Thr Phe Gly Gln Gly Thr Arg Leu Glu Ile Lys Gly Ser Thr Ser Gly
            100                 105                 110
Ser Gly Lys Pro Gly Ser Gly Glu Gly Ser Thr Lys Gly Gln Val Gln
            115                 120                 125
Leu Gln Gln Trp Gly Ala Gly Leu Leu Lys Pro Ser Glu Thr Leu Ser
    130                 135                 140
Leu Thr Cys Ala Val Tyr Gly Gly Ser Phe Ser Ala Tyr Tyr Trp Ser
145                 150                 155                 160
Trp Ile Arg Gln Pro Pro Gly Lys Gly Leu Glu Trp Ile Gly Asp Ile
                165                 170                 175
Asn His Gly Gly Gly Thr Asn Tyr Asn Pro Ser Leu Lys Ser Arg Val
            180                 185                 190
Thr Ile Ser Val Asp Thr Ser Lys Asn Gln Phe Ser Leu Lys Leu Asn
    195                 200                 205
Ser Val Thr Ala Ala Asp Thr Ala Val Tyr Tyr Cys Ala Ser Leu Thr
    210                 215                 220
Ala Tyr Trp Gly Gln Gly Ser Leu Val Thr Val Ser Ser Phe Val Pro
225                 230                 235                 240
Val Phe Leu Pro Ala Lys Pro Thr Thr Thr Pro Ala Pro Arg Pro Pro
                245                 250                 255
Thr Pro Ala Pro Thr Ile Ala Ser Gln Pro Leu Ser Leu Arg Pro Glu
            260                 265                 270
Ala Cys Arg Pro Ala Ala Gly Gly Ala Val His Thr Arg Gly Leu Asp
            275                 280                 285
Phe Ala Cys Asp Ile Tyr Ile Trp Ala Pro Leu Ala Gly Thr Cys Gly
    290                 295                 300
Val Leu Leu Leu Ser Leu Val Ile Thr Leu Tyr Cys Asn His Arg Asn
305                 310                 315                 320
Lys Arg Gly Arg Lys Lys Leu Leu Tyr Ile Phe Lys Gln Pro Phe Met
                325                 330                 335
Arg Pro Val Gln Thr Thr Gln Glu Glu Asp Gly Cys Ser Cys Arg Phe
            340                 345                 350
Pro Glu Glu Glu Glu Gly Gly Cys Glu Leu Arg Val Lys Phe Ser Arg
            355                 360                 365
Ser Ala Asp Ala Pro Ala Tyr Gln Gln Gly Gln Asn Gln Leu Tyr Asn
    370                 375                 380
Glu Leu Asn Leu Gly Arg Arg Glu Glu Tyr Asp Val Leu Asp Lys Arg
385                 390                 395                 400
Arg Gly Arg Asp Pro Glu Met Gly Gly Lys Pro Arg Arg Lys Asn Pro
                405                 410                 415
Gln Glu Gly Leu Tyr Asn Glu Leu Gln Lys Asp Lys Met Ala Glu Ala
            420                 425                 430
Tyr Ser Glu Ile Gly Met Lys Gly Glu Arg Arg Arg Gly Lys Gly His
            435                 440                 445
Asp Gly Leu Tyr Gln Gly Leu Ser Thr Ala Thr Lys Asp Thr Tyr Asp
    450                 455                 460
```

Ala Leu His Met Gln Ala Leu Pro Pro Arg
465                 470

<210> SEQ ID NO 19
<211> LENGTH: 5
<212> TYPE: PRT
<213> ORGANISM: Artificial Sequence
<220> FEATURE:
<223> OTHER INFORMATION: Synthetic

<400> SEQUENCE: 19

Arg Phe Val Ser Ser
1               5

<210> SEQ ID NO 20
<211> LENGTH: 1491
<212> TYPE: DNA
<213> ORGANISM: Artificial Sequence
<220> FEATURE:
<223> OTHER INFORMATION: Synthetic

<400> SEQUENCE: 20

```
gccaccatgg ccctgcctgt gacagctctg ctgctgcctc tggccctgct gctgcatgcc       60
gccagacccg atatccagat gacccagagc cccaccagcc tgtctgccag cgtgggcgac      120
agagtgacca tcacctgtag agccagccag ggcatcagca gctggctgac ctggtatcag      180
cagaagcccg agaaggcccc caagagcctg atctacgccg ccagctctct gcagtctggc      240
gtgcccagca gattttccgg cagcggctct ggcaccgact tcaccctgac aatcagcagc      300
ctgcagcccg aggacttcgc cacctactac tgccagcagt acgacagcta ccccatcacc      360
ttcggccagg gcacccggct ggaaatcaag gcagcacat ctggcagcgg caagcctgga      420
tctggcgagg gctctacaaa gggccaggtg cagctgcagc agtggggagc cggactgctg      480
aagcctagcg agacactgag cctgacctgc gccgtgtacg gcggcagctt cagcgcctac      540
tattggagct ggatccggca gcctcctggc aagggcctgg aatggatcgg cgacatcaat      600
cacggcggag gcaccaacta caacccccagc ctgaagtccc gcgtgaccat ctccgtggac      660
accagcaaga accagttctc cctgaagctg aacagcgtga cagccgccga cacagccgtg      720
tactactgtg ccagcctgac cgcctattgg ggccagggat ctctcgtgac cgtgtccagc      780
ttcgtgcccg tgttcctgcc tgccaagcct accacaaccc ctgccccctag acctcctacc      840
ccagccccta caatcgccag ccagcctctg tctctgaggc ccgaggcttg tagacctgct      900
gcaggcggag ccgtgcacac cagaggactg gatttcgcct gcgacatcta catctgggcc      960
cctctggccg gcacatgtgg cgtgctgctg ctgagcctcg tgatcaccct gtactgcaac     1020
caccggaaca gcggggcag aaagaagctg ctgtacatct tcaagcagcc cttcatgcgg     1080
cccgtgcaga ccacccagga agaggacggc tgctcctgca gattccccga ggaagaagaa     1140
ggcggctgcg agctgagagt gaagttcagc agatccgccg acgcccctgc ctaccagcag     1200
ggacagaacc agctgtacaa cgagctgaac ctgggcagac gggaagagta cgacgtgctg     1260
gacaagcgga gaggccggga ccccgagatg ggcggaaagc cagacggaa gaacccccag     1320
gaaggcctgt ataacgaact gcagaaagac aagatggccg aggcctacag cgagatcggc     1380
atgaagggcg agcggaggcg cggcaagggc cacgatggcc tgtaccaggg cctgagcacc     1440
gccaccaagg acacctacga cgccctgcac atgcaggccc tgcccccag a              1491
```

<210> SEQ ID NO 21
<211> LENGTH: 1437

<212> TYPE: DNA
<213> ORGANISM: Artificial Sequence
<220> FEATURE:
<223> OTHER INFORMATION: Synthetic

<400> SEQUENCE: 21

```
gccaccatgg ccctgcctgt gacagctctg ctgctgcctc tggccctgct gctgcatgcc      60
gccagacccg atatccagat gacccagagc cccaccagcc tgtctgccag cgtgggcgac     120
agagtgacca tcacctgtag agccagccag ggcatcagca gctggctgac ctggtatcag     180
cagaagcccg agaaggcccc caagagcctg atctacgccg ccagctctct gcagtctggc     240
gtgcccagca gattttccgg cagcggctct ggcaccgact tcaccctgac aatcagcagc     300
ctgcagcccg aggacttcgc cacctactac tgccagcagt acgacagcta ccccatcacc     360
ttcggccagg gcacccggct ggaaatcaag ggcagcacat ctggcagcgg caagcctgga     420
tctggcgagg gctctacaaa gggccaggtg cagctgcagc agtggggagc cggactgctg     480
aagcctagcg agacactgag cctgacctgc gccgtgtacg gcggcagctt cagcgcctac     540
tattggagct ggatccggca gcctcctggc aagggcctgg aatggatcgg cgacatcaat     600
cacggcggag gcaccaacta caaccccagc ctgaagtcca gagtgaccat cagcgtggac     660
accagcaaga accagttctc cctgaagctg aacagcgtga gcgccgccga caccgccgtg     720
tactactgtg ccagcctgac agcctattgg ggcagggct ctctcgtgac cgtgtccagc     780
atcgaagtga tgtacccccc tccctacctg gacaacgaga agtccaacgg caccatcatc     840
cacgtgaagg gcaagcacct gtgccccagc cctctgtttc ctggccctag caagcccttc     900
tgggtgctgg tggtcgtggg cggagtgctg gcctgttaca gcctgctcgt gacagtggcc     960
ttcatcatct tttgggtgcg cagcaagcgg agccggctgc tgcacagcga ctacatgaac    1020
atgacccccca gacggccagg ccccaccaga aagcactacc agccttacgc ccctcccaga    1080
gacttcgccg cctaccgcag cagagtgaag ttcagcagaa gcgccgacgc ccctgcctat    1140
cagcagggcc agaaccagct gtacaacgag ctgaacctgg gcagacggga agagtacgac    1200
gtgctggaca gcggagagg cagggaccct gagatgggcg gcaagcccag aagaaagaac    1260
ccccaggaag gcctgtataa cgaactgcag aaagacaaga tggccgaggc ctacagcgag    1320
atcggcatga agggcgagcg gagaagaggc aagggacacg acggcctgta ccagggactg    1380
agcaccgcca ccaaggacac ctacgacgcc ctgcacatgc aggccctgcc ccccaga       1437
```

<210> SEQ ID NO 22
<211> LENGTH: 1488
<212> TYPE: DNA
<213> ORGANISM: Artificial Sequence
<220> FEATURE:
<223> OTHER INFORMATION: Synthetic

<400> SEQUENCE: 22

```
gccaccatgg ccctgcctgt gacagctctg ctgctgcctc tggccctgct gctgcatgcc      60
gccagacccg atatccagat gacccagagc cccaccagcc tgtctgccag cgtgggcgac     120
agagtgacca tcacctgtag agccagccag ggcatcagca gctggctgac ctggtatcag     180
cagaagcccg agaaggcccc caagagcctg atctacgccg ccagctctct gcagtctggc     240
gtgcccagca gattttccgg cagcggctct ggcaccgact tcaccctgac aatcagcagc     300
ctgcagcccg aggacttcgc cacctactac tgccagcagt acgacagcta ccccatcacc     360
ttcggccagg gcacccggct ggaaatcaag ggcagcacat ctggcagcgg caagcctgga     420
```

```
tctggcgagg gctctacaaa gggccaggtg cagctgcagc agtggggagc cggactgctg    480
aagcctagcg agacactgag cctgacctgc gccgtgtacg gcggcagctt cagcgcctac    540
tattggagct ggatccggca gcctcctggc aagggcctgg aatggatcgg cgacatcaat    600
cacggcggag gcaccaacta caaccccagc ctgaagtccc gcgtgaccat ctccgtggac    660
accagcaaga accagttctc cctgaagctg aacagcgtga cagccgccga cacagccgtg    720
tactactgtg ccagcctgac cgcctattgg ggccagggat ctctcgtgac cgtgtccagc    780
ttcgtgcccg tgttcctgcc tgccaagcct accacaaccc ctgccctag acctcctacc    840 ccagccccta caatcgccag ccagcctctg tctctgaggc ccgaggcttg tagacctgct    900
gcaggcggag ccgtgcacac cagaggactg gatttcgcct gcgacatcta catctgggcc    960
cctctggccg gcacatgtgg cgtgctgctg ctgagcctcg tgatcaccct gtactgcaac   1020
caccggaaca gaagcaagcg gagccggctg ctgcacagcg actacatgaa catgacccca   1080
agacggcctg gccccacccg gaagcactac cagccttacg cccctcccag agacttcgcc   1140
gcctaccggt ccagagtgaa gttcagcaga tccgccgacg cccctgccta ccagcaggga   1200
cagaaccagc tgtacaacga gctgaacctg gcagacgggg aagagtacga cgtgctggac   1260
aagcggagag gccgggaccc cgagatgggc ggaaagccca gacggaagaa ccccaggaa    1320 ggcctgtata cgaactgca gaaagacaag atggccgagg cctacagcga gatcggcatg   1380
aagggcgagc ggaggcgcgg caagggccac gatggcctgt accagggcct gagcaccgcc   1440
accaaggaca cctacgacgc cctgcacatg caggccctgc cccccaga              1488
```

<210> SEQ ID NO 23
<211> LENGTH: 237
<212> TYPE: PRT
<213> ORGANISM: Artificial Sequence
<220> FEATURE:
<223> OTHER INFORMATION: Synthetic

<400> SEQUENCE: 23

```
Asp Ile Gln Met Thr Gln Ser Pro Thr Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Thr Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Ser Tyr Pro Ile
                85                  90                  95

Thr Phe Gly Gln Gly Thr Arg Leu Glu Ile Lys Gly Ser Thr Ser Gly
            100                 105                 110

Ser Gly Lys Pro Gly Ser Gly Glu Gly Ser Thr Lys Gly Gln Val Gln
        115                 120                 125

Leu Gln Gln Trp Gly Ala Gly Leu Leu Lys Pro Ser Glu Thr Leu Ser
    130                 135                 140

Leu Thr Cys Ala Val Tyr Gly Gly Ser Phe Ser Ala Tyr Tyr Trp Ser
145                 150                 155                 160

Trp Ile Arg Gln Pro Pro Gly Lys Gly Leu Glu Trp Ile Gly Asp Ile
                165                 170                 175
```

```
Asn His Gly Gly Gly Thr Asn Tyr Asn Pro Ser Leu Lys Ser Arg Val
            180                 185                 190

Thr Ile Ser Val Asp Thr Ser Lys Asn Gln Phe Ser Leu Lys Leu Asn
        195                 200                 205

Ser Val Thr Ala Ala Asp Thr Ala Val Tyr Tyr Cys Ala Ser Leu Thr
        210                 215                 220

Ala Tyr Trp Gly Gln Gly Ser Leu Val Thr Val Ser Ser
225                 230                 235
```

ANTI-CD30 CHIMERIC ANTIGEN RECEPTORS

CROSS-REFERENCE TO RELATED APPLICATIONS

This patent application is the U.S. national stage of International Patent Application Number PCT/US2016/056262, filed Oct. 10, 2016, which claims the benefit of U.S. Provisional Patent Application No. 62/241,896, filed Oct. 15, 2015, each of which is incorporated by reference in its entirety herein.

STATEMENT REGARDING FEDERALLY SPONSORED RESEARCH AND DEVELOPMENT

This invention was made with Government support under project number ZIABC01166003 by the National Institutes of Health, National Cancer Institute. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: one 28,009 Byte ASCII (Text) file named "738531_ST25.txt" dated Apr. 9, 2018.

BACKGROUND OF THE INVENTION

Cancer is a public health concern. Despite advances in treatments such as chemotherapy, the prognosis for many cancers, including lymphoma, may be poor. Accordingly, there exists an unmet need for additional treatments for cancer, particularly lymphoma.

BRIEF SUMMARY OF THE INVENTION

An embodiment of the invention provides a chimeric antigen receptor (CAR) having antigenic specificity for CD30, the CAR comprising: (a) an anti-CD30 antigen binding domain comprising a human heavy chain complementarity determining region (CDR) 1, a human heavy chain CDR2, a human heavy chain CDR3, a human light chain CDR1, a human light chain CDR2, and a human light chain CDR3; (b) a human hinge domain; (c) a human transmembrane domain; and (d) one or both of (i) a human intracellular T cell signaling domain and (ii) a human T cell costimulatory domain.

Further embodiments of the invention provide nucleic acids, recombinant expression vectors, host cells, populations of cells, and pharmaceutical compositions relating to the CARs of the invention.

Additional embodiments of the invention provide methods of treating or preventing a condition in a mammal, wherein the condition is cancer.

DETAILED DESCRIPTION OF THE INVENTION

Figure 1:
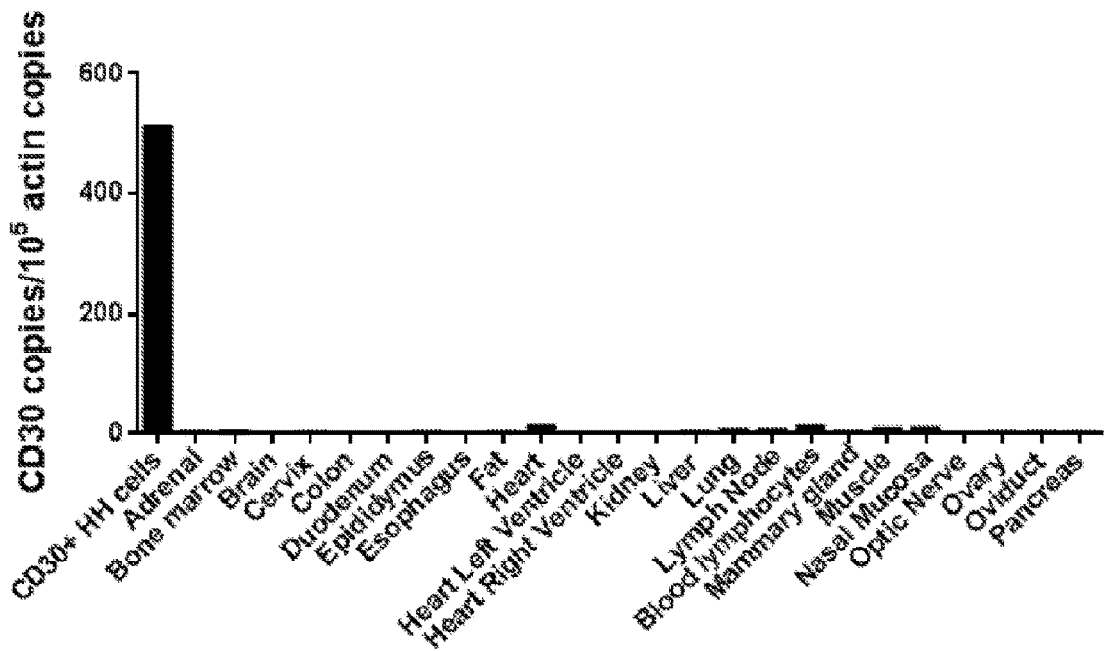
FIGS. 1A and 1B are graphs showing the number of CD30 cDNA copies per $10^5$ copies of β-actin cDNA measured by qPCR in the CD30+ HH lymphoma cell line (positive control) or in the indicated normal tissues.
Figure 1:
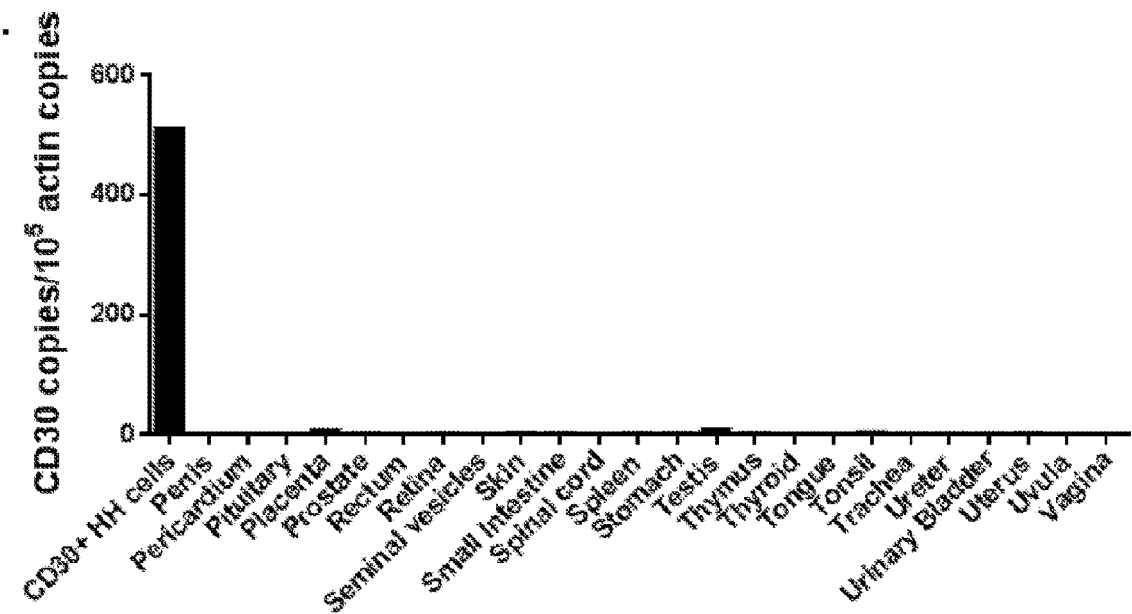

An embodiment of the invention provides a CAR having antigenic specificity for CD30, the CAR comprising: (a) an anti-CD30 antigen binding domain comprising a human heavy chain complementarity determining region (CDR) 1, a human heavy chain CDR2, a human heavy chain CDR3, a human light chain CDR1, a human light chain CDR2, and a human light chain CDR3; (b) a human hinge domain; (c) a human transmembrane (TM) domain; and (d) one or both of (i) a human intracellular T cell signaling domain and (ii) a human T cell costimulatory domain.

A CAR is an artificially constructed hybrid protein or polypeptide containing the antigen binding domains of an antibody (e.g., single chain variable fragment (scFv)) linked to T-cell signaling domains. Characteristics of CARs include their ability to redirect T-cell specificity and reactivity toward a selected target in a non-MHC-restricted manner, exploiting the antigen-binding properties of monoclonal antibodies. The non-MHC-restricted antigen recognition gives cells expressing CARs the ability to recognize antigen independent of antigen processing, thus bypassing a major mechanism of tumor escape. Moreover, when expressed in T-cells, CARs advantageously do not dimerize with endogenous T cell receptor (TCR) alpha and beta chains.

The inventive CARs may provide many advantages. For example, all or nearly all of the components of the inventive CARs may be human sequences. Accordingly, administration of the inventive CARs to a human patient may be less likely to cause an undesirable immune response against the CAR in the human patient as compared to CARs that contain non-human sequences, e.g., mouse sequences.

The CARs of the invention have antigenic specificity for human CD30 (also known as tumor necrosis factor receptor superfamily, member 8 (TNFRSF8)). CD30 is expressed or overexpressed by a variety of human cancer cells, including lymphomas. Examples of cancers that express or overexpress CD30 include, but are not limited to, B-cell lymphoma (such as, for example, diffuse large B cell lymphoma (DLBCL), primary mediastinal B-cell lymphoma (PMBL), Hodgkin lymphoma (HL), non-Hodgkin lymphoma, mediastinal gray zone lymphoma, and nodular sclerosis HL) and T-cell lymphoma (such as, for example, anaplastic large cell lymphoma (ALCL), peripheral T cell lymphoma not otherwise specified (PTCL-NOS), and angioimmunoblastic T cell lymphoma (AITL)). Without being bound to a particular theory or mechanism, it is believed that by eliciting an antigen-specific response against CD30, the inventive CARs provide for one or more of the following: targeting and destroying CD30-expressing cancer cells, reducing or eliminating cancer cells, facilitating infiltration of immune cells to tumor site(s), and enhancing/extending anti-cancer responses.

The phrases "have antigen(ic) specificity" and "elicit antigen-specific response," as used herein, mean that the CAR can specifically bind to and immunologically recognize antigen (CD30), such that binding of the CAR to the antigen elicits an immune response.

An embodiment of the invention provides a CAR comprising the antigen binding domain of the 5F11 human antibody ("5F11"). The antigen binding domain of 5F11 specifically binds to CD30. The 5F11 antibody is described in U.S. Pat. No. 7,387,776, which is incorporated herein by reference.

The antigen binding domain may comprise any antigen binding portion of the 5F11 antibody. For example, the antigen binding domain may be a Fab fragment (Fab), F(ab')$_2$ fragment, diabody, triabody, tetrabody, single-chain variable region fragment (scFv), or a disulfide-stabilized variable region fragment (dsFv). In a preferred embodiment, the antigen binding domain is an scFv. An scFv is a truncated Fab fragment including the variable (V) domain of an antibody heavy chain linked to a V domain of an antibody light chain via a synthetic peptide, which can be generated using routine recombinant DNA technology techniques. The anti-CD30 antigen binding domain employed in the inventive CARs, however, is not limited to these exemplary types of antibody fragments.

The antigen binding domain may comprise a light chain variable region and/or a heavy chain variable region. In an embodiment of the invention, the heavy chain variable region comprises a complementarity determining region (CDR) 1, a CDR2, and a CDR3. In a preferred embodiment, the antigen binding domain comprises a human heavy chain CDR1, a human heavy chain CDR2, and a human heavy chain CDR3. In this regard, the antigen binding domain may comprise one or more of a heavy chain CDR1 comprising, consisting of, or consisting essentially of the amino acid sequence of SEQ ID NO: 1; a heavy chain CDR2 comprising, consisting of, or consisting essentially of the amino acid sequence of SEQ ID NO: 2; and a heavy chain CDR3 comprising, consisting of, or consisting essentially of the amino acid sequence of SEQ ID NO: 3. Preferably, the heavy chain comprises all of the amino acid sequences of SEQ ID NOs: 1-3.

In an embodiment of the invention, the light chain variable region may comprise a light chain CDR1, a light chain CDR2, and a light chain CDR3. In a preferred embodiment, the antigen binding domain comprises a human light chain CDR1, a human light chain CDR2, and a human light chain CDR3. In this regard, the antigen binding domain may comprise one or more of a light chain CDR1 comprising, consisting of, or consisting essentially of the amino acid sequence of SEQ ID NO: 4; a light chain CDR2 comprising, consisting of, or consisting essentially of the amino acid sequence of SEQ ID NO: 5; and a light chain CDR3 comprising, consisting of, or consisting essentially of the amino acid sequence of SEQ ID NO: 6. Preferably, the light chain comprises the amino acid sequences of all of SEQ ID NOs: 4-6. In an especially preferred embodiment, the antigen binding domain comprises all of the amino acid sequences of SEQ ID NO: 1-6.

In an embodiment of the invention, the antigen binding domain comprises a heavy chain variable region and a light chain variable region. In a preferred embodiment, the antigen binding domain comprises a human heavy chain variable region and a human light chain variable region. The heavy chain variable region of the antigen binding domain may comprise, consist of, or consist essentially of the amino acid sequence of SEQ ID NO: 7. The light chain variable region of the antigen binding domain may comprise, consist of, or consist essentially of the amino acid sequence of SEQ ID NO: 8. Accordingly, in an embodiment of the invention, the antigen binding domain comprises a heavy chain variable region comprising the amino acid sequence of SEQ ID NO: 7 and/or a light chain variable region comprising the amino acid sequence of SEQ ID NO: 8. Preferably, the antigen binding domain comprises the amino acid sequences of both SEQ ID NOs: 7 and 8.

In an embodiment of the invention, the light chain variable region and the heavy chain variable region may be joined by a linker. The linker may comprise any suitable amino acid sequence. In an embodiment of the invention, the linker may comprise, consist, or consist essentially of, SEQ ID NO: 10. In an embodiment of the invention, the antigen binding domain comprises an scFv comprising the amino acid sequence of SEQ ID NO: 23.

In an embodiment of the invention, the antigen binding domain comprises a leader sequence. The leader sequence may be positioned at the amino terminus of the light chain variable region or the heavy chain variable region. Preferably, the leader sequence is positioned at the amino terminus of the light chain variable region. The leader sequence may comprise any suitable leader sequence. For example, the antigen binding domain may comprise a leader sequence comprising, consisting of, or consisting essentially of SEQ ID NO: 9. In an embodiment of the invention, while the leader sequence may facilitate expression of the CAR on the surface of the cell, the presence of the leader sequence in an expressed CAR may not be necessary in order for the CAR to function. In an embodiment of the invention, upon expression of the CAR on the cell surface, all or a portion of the leader sequence may be cleaved off of the CAR. Accordingly, in an embodiment of the invention, the CAR lacks a leader sequence.

In an embodiment of the invention, the CAR comprises a hinge domain and a transmembrane (TM) domain. Preferably, the hinge domain is a human hinge domain and the TM domain is a human TM domain. The hinge domain and the TM domain may comprise the hinge domain and the TM domain of human CD8α. In this regard, the hinge domain and the TM domain of human CD8α may comprise, consist, or consist essentially of the amino acid sequence of SEQ ID NO: 11.

In an embodiment of the invention, the CAR comprises an intracellular T cell signaling domain. Preferably, the intracellular T cell signaling domain is a human intracellular T cell signaling domain. The intracellular T cell signaling domain may comprise an intracellular T cell signaling domain of one or more of human CD28, human 4-1BB, and human CD3ζ. CD28 is a T cell marker important in T cell co-stimulation. The intracellular T cell signaling domain of human CD28 may comprise, consist, or consist essentially of the amino acid sequence of SEQ ID NO: 12. 4-1BB, also referred to as CD137, transmits a potent costimulatory signal to T cells, promoting differentiation and enhancing long-term survival of T lymphocytes. The intracellular T cell signaling domain of human 4-1BB may comprise, consist, or consist essentially of the amino acid sequence of SEQ ID NO: 14. CD3ζ associates with TCRs to produce a signal and contains immunoreceptor tyrosine-based activation motifs (ITAMs). The intracellular T cell signaling domain of human CD3ζ may comprise, consist, or consist essentially of the amino acid sequence of SEQ ID NO: 15.

In an embodiment of the invention, the CAR comprises (i) the hinge domain and the TM domain of human CD8α; (ii) the intracellular T cell signaling domain of human CD28; and (iii) the intracellular T cell signaling domain of human CD3ζ. In this regard, the CAR may comprise the amino acid sequences of all of SEQ ID NOs: 11-12 and 15. The CAR comprising the amino acid sequences of all of SEQ ID NOs: 11-12 and 15 may further comprise an antigen binding domain as described herein with respect to other aspects of the invention. In this regard, the CAR may comprise the amino acid sequences of (i) SEQ ID NOs: 1-6, 11-12, and 15; (ii) SEQ ID NOs: 7-8, 11-12, and 15; or (iii) SEQ ID NO: 23, 11-12, and 15.

In an embodiment of the invention, the CAR comprises (i) the hinge domain and the TM domain of human CD8α; (ii) the intracellular T cell signaling domain of human 4-1BB; and (iii) the intracellular T cell signaling domain of human CD3ζ. In this regard, the CAR may comprise the amino acid sequences of all of SEQ ID NOs: 11 and 14-15. The CAR comprising the amino acid sequences of all of SEQ ID NOs: 11 and 14-15 may further comprise an antigen binding domain as described herein with respect to other aspects of the invention. In this regard, the CAR may comprise the amino acid sequences of (i) SEQ ID NOs: 1-6, 11 and 14-15; (ii) SEQ ID NOs: 7-8, 11 and 14-15; or (iii) SEQ ID NO: 23, 11 and 14-15.

In an embodiment of the invention, the CAR comprises (i) a hinge domain, a TM domain, and an intracellular T cell signaling domain of human CD28 and (ii) an intracellular T cell signaling domain of human CD3ζ. The hinge domain, the TM domain, and the intracellular T cell signaling domain of human CD28 may comprise, consist, or consist essentially of the amino acid sequence of SEQ ID NO: 13. The intracellular T cell signaling domain of human CD3ζ may comprise, consist, or consist essentially of the amino acid sequence of SEQ ID NO: 15. In this regard, the CAR may comprise the amino acid sequences of both of SEQ ID NOs: 13 and 15. The CAR comprising the amino acid sequences of both of SEQ ID NOs: 13 and 15 may further comprise an antigen binding domain as described herein with respect to other aspects of the invention. In this regard, the CAR may comprise the amino acid sequences of (i) SEQ ID NOs: 1-6, 13, and 15; (ii) SEQ ID NOs: 7-8, 13, and 15; or (iii) SEQ ID NO: 23, 13, and 15.

An embodiment of the invention provides a CAR comprising the amino acid sequence of any one of SEQ ID NOs: 16-18. The components of the CARs comprising the amino acid sequence of any one of SEQ ID NOs: 16-18 are set forth in Table 1.

TABLE 1

| SEQ ID NO: | Antigen Binding Domain | Further Components |
|---|---|---|
| SEQ ID NO: 16 | 5F11 scFv (SEQ ID NO: 23) | (i) a hinge domain, a TM domain, and an intracellular T cell signaling domain of human CD28 (SEQ ID NO: 13); and (ii) an intracellular T cell signaling domain of human CD3ζ (SEQ ID NO: 15) |
| SEQ ID NO: 17 | 5F11 scFv (SEQ ID NO: 23) | (i) hinge domain and TM domain of human CD8α (SEQ ID NO: 11); (ii) intracellular T cell signaling domain of human CD28 (SEQ ID NO: 12); and (iii) intracellular T cell signaling domain of human CD3ζ (SEQ ID NO: 15) |
| SEQ ID NO: 18 | 5F11 scFv (SEQ ID NO: 23) | (i) hinge domain and TM domain of human CD8α (SEQ ID NO: 11); (ii) intracellular T cell signaling domain of human 4-1BB (SEQ ID NO: 14); and (iii) intracellular T cell signaling domain of human CD3ζ (SEQ ID NO: 15) |

Included in the scope of the invention are functional variants of the inventive CARs described herein. The term "functional variant," as used herein, refers to a CAR having substantial or significant sequence identity or similarity to a parent CAR, which functional variant retains the biological activity of the CAR of which it is a variant. Functional variants encompass, for example, those variants of the CAR described herein (the parent CAR) that retain the ability to recognize target cells to a similar extent, the same extent, or to a higher extent, as the parent CAR. In reference to the parent CAR, the functional variant can, for instance, be at least about 30%, about 50%, about 75%, about 80%, about 85%, about 90%, about 91%, about 92%, about 93%, about 94%, about 95%, about 96%, about 97%, about 98%, about 99% or more identical in amino acid sequence to the parent CAR.

A functional variant can, for example, comprise the amino acid sequence of the parent CAR with at least one conservative amino acid substitution. Alternatively or additionally, the functional variants can comprise the amino acid sequence of the parent CAR with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent CAR.

Amino acid substitutions of the inventive CARs are preferably conservative amino acid substitutions. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic/negatively charged polar amino acid substituted for another acidic/negatively charged polar amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Cys, Val, etc.), a basic/positively charged polar amino acid substituted for another basic/positively charged polar amino acid (e.g. Lys, His, Arg, etc.), an uncharged amino acid with a polar side chain substituted for another uncharged amino acid with a polar side chain (e.g., Asn, Gln, Ser, Thr, Tyr, etc.), an amino acid with a beta-branched side-chain substituted for another amino acid with a beta-branched side-chain (e.g., Ile, Thr, and Val), an amino acid with an aromatic side-chain substituted for another amino acid with an aromatic side chain (e.g., His, Phe, Trp, and Tyr), etc.

The CAR can consist essentially of the specified amino acid sequence or sequences described herein, such that other components, e.g., other amino acids, do not materially change the biological activity of the CAR.

The CARs of embodiments of the invention can be of any length, i.e., can comprise any number of amino acids, provided that the CARs retain their biological activity, e.g., the ability to specifically bind to antigen or treat or prevent a condition in a mammal, etc. For example, the CAR can be about 50 to about 5000 amino acids long, such as 50, 70, 75, 100, 125, 150, 175, 200, 300, 400, 500, 600, 700, 800, 900, 1000 or more amino acids in length.

The CARs of embodiments of the invention can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

The CARs of embodiments of the invention can be glycosylated, amidated, carboxylated, phosphorylated, esterified, N-acylated, cyclized via, e.g., a disulfide bridge, or converted into an acid addition salt and/or optionally dimerized or polymerized.

The CARs of embodiments of the invention can be obtained by methods known in the art. The CARs may be made by any suitable method of making polypeptides or proteins. Suitable methods of de novo synthesizing polypeptides and proteins are known in the art. Also, the CARs can be recombinantly produced using the nucleic acids described herein using standard recombinant methods as described in, for example, Green and Sambrook, *Molecular Cloning: A Laboratory Manual* (4$^{th}$ Ed.), Cold Spring Harbor Laboratory Press (2012). Alternatively, the CARs described herein can be commercially synthesized by companies, such as, for example, Synpep (Dublin, Calif.) and Multiple Peptide Systems (San Diego, Calif.). In this respect, the inventive CARs can be synthetic and/or recombinant.

Further provided by an embodiment of the invention is a nucleic acid comprising a nucleotide sequence encoding any of the CARs described herein. The nucleic acids of the invention may comprise a nucleotide sequence encoding any one or more of the leader sequences, linkers, antigen binding domains, TM domains, and intracellular T cell signaling domains described herein. In an embodiment of the invention, the nucleic acid comprises any one of the nucleotide sequences set forth in Table 2.

TABLE 2

| Nucleotide SEQ ID NO: | Amino Acid SEQ ID NO: | Antigen Binding Domain | Further Components |
|---|---|---|---|
| SEQ ID NO: 21 | SEQ ID NO: 16 | 5F11 scFv (SEQ ID NO: 23) | (i) a hinge domain, a TM domain, and an intracellular T cell signaling domain of human CD28 (SEQ ID NO: 13); and (ii) an intracellular T cell signaling domain of human CD3ζ (SEQ ID NO: 15) |

TABLE 2-continued

| Nucleotide SEQ ID NO: | Amino Acid SEQ ID NO: | Antigen Binding Domain | Further Components |
|---|---|---|---|
| SEQ ID NO: 22 | SEQ ID NO: 17 | 5F11 scFv (SEQ ID NO: 23) | (i) hinge domain and TM domain of human CD8α (SEQ ID NO: 11); (ii) intracellular T cell signaling domain of human CD28 (SEQ ID NO: 12); and (iii) intracellular T cell signaling domain of human CD3ζ (SEQ ID NO: 15) |
| SEQ ID NO: 20 | SEQ ID NO: 18 | 5F11 scFv (SEQ ID NO: 23) | (i) hinge domain and TM domain of human CD8α (SEQ ID NO: 11); (ii) intracellular T cell signaling domain of human 4-1BB (SEQ ID NO: 14); and (iii) intracellular T cell signaling domain of human CD3ζ (SEQ ID NO: 15) |

"Nucleic acid," as used herein, includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In some embodiments, the nucleic acid does not comprise any insertions, deletions, inversions, and/or substitutions. However, it may be suitable, in some instances, for the nucleic acid to comprise one or more insertions, deletions, inversions, and/or substitutions.

The nucleic acids of an embodiment of the invention may be recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids can consist essentially of the specified nucleotide sequence or sequences described herein, such that other components, e.g., other nucleotides, do not materially change the biological activity of the encoded CAR.

A recombinant nucleic acid may be one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques, such as those described in Green et al., supra. The nucleic acids can be constructed based on chemical synthesis and/or enzymatic ligation reactions using procedures known in the art. See, for example, Green et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as, for example, Macromolecular Resources (Fort Collins, Colo.) and Synthegen (Houston, Tex.).

The nucleic acid can comprise any isolated or purified nucleotide sequence which encodes any of the CARs described herein. Alternatively, the nucleotide sequence can comprise a nucleotide sequence which is degenerate to any of the sequences or a combination of degenerate sequences.

An embodiment of the invention also provides an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions may hybridize under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive CARs described herein. It is generally appreciated that conditions can be rendered more stringent by the addition of increasing amounts of formamide.

In an embodiment of the invention, the nucleic acid comprises a codon-optimized nucleotide sequence encoding the CAR. Without being bound to any particular theory or mechanism, it is believed that codon optimization of the nucleotide sequence increases the translation efficiency of the mRNA transcripts. Codon optimization of the nucleotide sequence may involve substituting a native codon for another codon that encodes the same amino acid, but can be translated by tRNA that is more readily available within a cell, thus increasing translation efficiency. Optimization of the nucleotide sequence may also reduce secondary mRNA structures that would interfere with translation, thus increasing translation efficiency. In this regard, the nucleic acid encoding a CAR may comprise the codon-optimized nucleotide sequence of any one of SEQ ID NOs: 20-22.

The invention also provides a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to the nucleotide sequence of any of the nucleic acids described herein.

In an embodiment, the nucleic acids of the invention can be incorporated into a recombinant expression vector. In this regard, an embodiment of the invention provides recombinant expression vectors comprising any of the nucleic acids of the invention. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring or non-naturally-occurring internucleotide linkages, or both types of linkages. Preferably, the non-naturally occurring or altered nucleotides or internucleotide linkages do not hinder the transcription or replication of the vector.

In an embodiment, the recombinant expression vector of the invention can be any suitable recombinant expression vector, and can be used to transform or transfect any suitable host cell. Suitable vectors include those designed for propagation and expansion or for expression or both, such as plasmids and viruses. The vector can be selected from the group consisting of the pUC series (Fennentas Life Sciences, Glen Burnie, Md.), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and XNM1149, also can be used. Examples of plant expression vectors include pBI01, pBI101.2, pBI101.3, pBI121 and pBIN19 (Clontech). Examples of animal expression vectors include pEUK-Cl, pMAM, and pMAMneo (Clontech). The recombinant expression vector may be a viral vector, e.g., a retroviral vector. In an embodiment of the invention, the vector is a gamma-retroviral vector, a lentiviral vector, or a transposon.

In an embodiment, the recombinant expression vectors of the invention can be prepared using standard recombinant DNA techniques described in, for example, Green et al., supra. Constructs of expression vectors, which are circular or linear, can be prepared to contain a replication system functional in a prokaryotic or eukaryotic host cell. Replication systems can be derived, e.g., from ColE1, 2µ plasmid, λ, SV40, bovine papilloma virus, and the like.

The recombinant expression vector may comprise regulatory sequences, such as transcription and translation initiation and termination codons, which are specific to the type of host cell (e.g., bacterium, fungus, plant, or animal) into which the vector is to be introduced, as appropriate, and taking into consideration whether the vector is DNA- or RNA-based. The recombinant expression vector may comprise restriction sites to facilitate cloning.

The recombinant expression vector can include one or more marker genes, which allow for selection of transformed or transfected host cells. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the inventive CARs, or to the nucleotide sequence which is complementary to or which hybridizes to the nucleotide sequence encoding the inventive CARs. The selection of promoters, e.g., strong, weak, inducible, tissue-specific and developmental-specific, is within the ordinary skill of the artisan. Similarly, the combining of a nucleotide sequence with a promoter is also within the ordinary skill of the artisan. The promoter can be a non-viral promoter or a viral promoter, e.g., a cytomegalovirus (CMV) promoter, an SV40 promoter, an RSV promoter, or a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression.

Further, the recombinant expression vectors can be made to include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art and include, for example, the Herpes Simplex Virus (HSV) thymidine kinase (TK) gene, cytosine daminase, purine nucleoside phosphorylase, and nitroreductase.

An embodiment of the invention further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5α *E. coli* cells, Chinese hamster ovarian cells, monkey VERO cells, COS cells, HEK293 cells, and the like. For purposes of amplifying or replicating the recombinant expression vector, the host cell may be a prokaryotic cell, e.g., a DH5α cell. For purposes of producing a CAR, the host cell may be a mammalian cell. The host cell may be a human cell. While the host cell can be of any cell type, can originate from any type of tissue, and can be of any developmental stage, the host cell may be a peripheral blood lymphocyte (PBL) or a peripheral blood mononuclear cell (PBMC). The host cell may be a B cell, a natural killer (NK) cell, or a T cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. The T cell may be a human T cell. The T cell may be a T cell isolated from a human. The T cell can be any type of T cell and can be of any developmental stage, including but not limited to, $CD4^+/CD8^+$ double positive T cells, $CD4^+$ helper T cells, e.g., $Th_1$ and $Th_2$ cells, $CD8^+$ T cells (e.g., cytotoxic T cells), tumor infiltrating cells, memory T cells, naïve T cells, and the like. The T cell may be a $CD8^+$ T cell or a $CD4^+$ T cell.

Also provided by an embodiment of the invention is a population of cells comprising at least two of the host cells described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cell, a muscle cell, a brain cell, etc. Alternatively, the population of cells can be a substantially homogeneous population, in which the population comprises mainly host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

In an embodiment of the invention, the number of cells in the population may be rapidly expanded. Expansion of the numbers of cells expressing the CAR can be accomplished by any of a number of methods as are known in the art as described in, for example, U.S. Pat. Nos. 8,034,334; 8,383,099; U.S. Patent Application Publication No. 2012/0244133; Dudley et al., *J. Immunother.*, 26:332-42 (2003); and Riddell et al., *J. Immunol. Methods*, 128:189-201 (1990). In an embodiment, expansion of the numbers of cells is carried out by culturing the T cells with OKT3 antibody, IL-2, and feeder PBMC (e.g., irradiated allogeneic PBMC).

The CARs, functional variants, nucleic acids, recombinant expression vectors, and host cells (including populations thereof), all of which are collectively referred to as "inventive anti-CD30 materials" hereinafter, can be isolated and/or purified. The term "isolated," as used herein, means having been removed from its natural environment. The term "purified" or "isolated" does not require absolute purity or isolation; rather, it is intended as a relative term. Thus, for example, a purified (or isolated) host cell preparation is one in which the host cell is more pure than cells in their natural environment within the body. Such host cells may be produced, for example, by standard purification techniques. In some embodiments, a preparation of a host cell is purified such that the host cell represents at least about 50%, for example, at least about 70%, of the total cell content of the preparation. For example, the purity can be at least about 50%, can be greater than about 60%, about 70% or about 80%, or can be about 100%.

The inventive anti-CD30 materials can be formulated into a composition, such as a pharmaceutical composition. In this regard, an embodiment of the invention provides a pharmaceutical composition comprising any of the inventive anti-CD30 materials described herein and a pharmaceutically acceptable carrier. The inventive pharmaceutical compositions containing any of the inventive anti-CD30 materials can comprise more than one inventive anti-CD30 material, e.g., a CAR and a nucleic acid. Alternatively, the pharmaceutical composition can comprise an inventive CAR material in combination with other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. In a preferred embodiment, the pharmaceutical composition comprises the inventive host cell or populations thereof.

Preferably, the carrier is a pharmaceutically acceptable carrier. With respect to pharmaceutical compositions, the carrier can be any of those conventionally used for the particular inventive CAR material under consideration. Methods for preparing administrable compositions are known or apparent to those skilled in the art and are described in more detail in, for example, *Remington: The Science and Practice of Pharmacy*, $22^{nd}$ Ed., Pharmaceutical Press (2012). It is preferred that the pharmaceutically acceptable carrier be one which has no detrimental side effects or toxicity under the conditions of use.

The choice of carrier will be determined in part by the particular inventive CAR material, as well as by the particular method used to administer the inventive CAR material. Accordingly, there are a variety of suitable formulations of the pharmaceutical composition of the invention. Suitable formulations may include any of those for parenteral, subcutaneous, intravenous, intramuscular, intraarterial, intrathecal, intratumoral, or interperitoneal administration. More than one route can be used to administer the inventive CAR materials, and in certain instances, a particular route can provide a more immediate and more effective response than another route.

Preferably, the inventive CAR material is administered by injection, e.g., intravenously. When the inventive CAR material is a host cell (or a population thereof) expressing the inventive CAR, the pharmaceutically acceptable carrier for the cells for injection may include any isotonic carrier such as, for example, normal saline (about 0.90% w/v of NaCl in water, about 300 mOsm/L NaCl in water, or about 9.0 g NaCl per liter of water), NORMOSOL R electrolyte solution (Abbott, Chicago, Ill.), PLASMA-LYTE A (Baxter, Deerfield, Ill.), about 5% dextrose in water, or Ringer's lactate. In an embodiment, the pharmaceutically acceptable carrier is supplemented with human serum albumen.

An "effective amount" or "an amount effective to treat" refers to a dose that is adequate to prevent or treat cancer in an individual. Amounts effective for a therapeutic or prophylactic use will depend on, for example, the stage and severity of the condition being treated, the age, weight, and general state of health of the patient, and the judgment of the prescribing physician. The size of the dose will also be determined by the anti-CD30 material selected, method of administration, timing and frequency of administration, the existence, nature, and extent of any adverse side-effects that might accompany the administration of a particular anti-CD30 material, and the desired physiological effect. It will be appreciated by one of skill in the art that various conditions (e.g., cancer) could require prolonged treatment involving multiple administrations, perhaps using the inventive anti-CD30 material(s) in each or various rounds of administration.

The dose of the inventive CAR material also will be determined by the existence, nature and extent of any adverse side effects that might accompany the administration of a particular inventive CAR material. Typically, the attending physician will decide the dosage of the inventive CAR material with which to treat each individual patient, taking into consideration a variety of factors, such as age, body weight, general health, diet, sex, inventive CAR material to be administered, route of administration, and the severity of the condition being treated. In an embodiment in which the inventive CAR material is a population of cells, the number of cells administered per infusion may vary, e.g., from about $1 \times 10^6$ to about $1 \times 10^{12}$ cells or more.

For purposes of the invention, the amount or dose of the inventive anti-CD30 material administered should be sufficient to effect a therapeutic or prophylactic response in the subject or mammal over a reasonable time frame. For example, the dose of the inventive anti-CD30 material should be sufficient to bind to CD30 or treat or prevent a condition in a period of from about 2 hours or longer, e.g., about 12 to about 24 or more hours, from the time of administration. In certain embodiments, the time period could be even longer. The dose will be determined by the efficacy of the particular inventive anti-CD30 material and the condition of the mammal (e.g., human), as well as the body weight of the mammal (e.g., human) to be treated.

For purposes of the invention, an assay, which comprises, for example, comparing the extent to which target cells are lysed and/or IFN-γ is secreted by T cells expressing the inventive CAR upon administration of a given dose of such T cells to a mammal, among a set of mammals of which each is given a different dose of the T cells, could be used to determine a starting dose to be administered to a mammal. The extent to which target cells are lysed and/or IFN-γ is secreted upon administration of a certain dose can be assayed by methods known in the art.

When the inventive anti-CD30 material(s) are administered with one or more additional therapeutic agents, one or more additional therapeutic agents can be coadministered to the mammal. By "coadministering" is meant administering one or more additional therapeutic agents and the inventive CAR material(s) sufficiently close in time such that the inventive anti-CD30 material(s) can enhance the effect of one or more additional therapeutic agents, or vice versa. In this regard, the inventive anti-CD30 material(s) can be administered first and the one or more additional therapeutic agents can be administered second, or vice versa. Alternatively, the inventive anti-CD30 material(s) and the one or more additional therapeutic agents can be administered simultaneously. Additional therapeutic agents that may enhance CAR-expressing cell function may include, for example, one or more cytokines or one or more antibodies (e.g., antibodies that inhibit PD-1 function). An exemplary therapeutic agent that can be co-administered with the anti-CD30 material(s) is IL-2. Without being bound to a particular theory or mechanism, it is believed that IL-2 may enhance the therapeutic effect of the inventive anti-CD30 material(s).

It is contemplated that the inventive anti-CD30 materials and pharmaceutical compositions can be used in methods of treating or preventing a condition in a mammal. Without being bound to a particular theory or mechanism, the inventive anti-CD30 CARs have biological activity, e.g., ability to recognize CD30, such that the anti-CD30 CAR, when expressed by a cell, is able to mediate an immune response against the cell expressing the CD30, for which the anti-CD30 CAR is specific. In this regard, an embodiment of the invention provides a method of treating or preventing a condition in a mammal, comprising administering to the mammal any of the CARs, nucleic acids, recombinant expression vectors, host cells, population of cells, and/or pharmaceutical compositions of the invention in an amount effective to treat or prevent the condition in the mammal. The condition may be any condition characterized by the expression or overexpression of CD30. In a preferred embodiment, the condition is cancer.

An embodiment of the invention further comprises lymphodepleting the mammal prior to administering the inventive anti-CD30 material(s). Examples of lymphodepletion include, but may not be limited to, nonmyeloablative lymphodepleting chemotherapy, myeloablative lymphodepleting chemotherapy, total body irradiation, etc.

For purposes of the inventive methods, wherein host cells or populations of cells are administered, the cells can be cells that are allogeneic or autologous to the mammal. Preferably, the cells are autologous to the mammal.

The mammal referred to herein can be any mammal. As used herein, the term "mammal" refers to any mammal, including, but not limited to, mammals of the order Rodentia, such as mice and hamsters, and mammals of the order Logomorpha, such as rabbits. The mammals may be from the order Carnivora, including Felines (cats) and Canines (dogs). The mammals may be from the order Artiodactyla, including Bovines (cows) and Swines (pigs) or of the order Perssodactyla, including Equines (horses). The mammals may be of the order Primates, Ceboids, or Simoids (monkeys) or of the order Anthropoids (humans and apes). Preferably, the mammal is a human.

With respect to the inventive methods, the cancer can be any cancer. Preferably, the cancer is lymphoma. In an especially preferred embodiment, the cancer is a B-cell lymphoma (such as, for example, diffuse large B cell lymphoma (DLBCL), primary mediastinal B-cell lymphoma (PMBL), Hodgkin lymphoma (HL), non-Hodgkin lymphoma, mediastinal gray zone lymphoma, and nodular sclerosis HL) or a T-cell lymphoma (such as, for example, anaplastic large cell lymphoma (ALCL), peripheral T cell lymphoma not otherwise specified (PTCL-NOS), angioimmunoblastic T cell lymphoma (AITL), and other T cell lymphomas). Preferably, the cancer is characterized by the expression or overexpression of CD30.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of a condition in a mammal. Furthermore, the treatment or prevention provided by the inventive method can include treatment or prevention of one or more conditions or symptoms of the condition, e.g., cancer, being treated or prevented. Also, for purposes herein, "prevention" can encompass delaying the onset of the condition, e.g., cancer, or a symptom or condition thereof. Alternatively or additionally, "prevention" can encompass delaying the recurrence of the condition, e.g., cancer, or a symptom or condition thereof.

In an embodiment of the invention, a nucleic acid encoding the inventive CAR is introduced into any of the vectors described herein. The vector may then, in turn, be introduced into any of the host cells described herein (e.g., NK cells or T cells) by any suitable technique such as, e.g., gene editing, transfection, transformation, or transduction. Many transfection techniques are known in the art and include, for example, calcium phosphate DNA co-precipitation; DEAE-dextran; electroporation; cationic liposome-mediated transfection; tungsten particle-facilitated microparticle bombardment; and strontium phosphate DNA co-precipitation. Phage or viral vectors can be introduced into host cells, after growth of infectious particles in suitable packaging cells, many of which are commercially available.

One or more isolated host cells (e.g., NK cells or T cells), into which a vector encoding the inventive CAR has been introduced, can be cultured ex vivo under conditions to express the inventive anti-CD30 CAR, and then directly transferred into a mammal (preferably a human) affected by a CD30-expressing cancer. Such a cell transfer method is referred to in the art as "adoptive cell transfer (ACT)."

When host cells (e.g., T-cells or NK cells) are administered to a mammal, the cells can be allogeneic or autologous to the mammal. In "autologous" administration methods, cells are removed from a mammal, stored (and optionally modified), and returned back to the same mammal. In "allogeneic" administration methods, a mammal receives cells from a genetically similar, but not identical, donor. Preferably, the cells are autologous to the mammal. In an embodiment of the invention, the cells administered to the mammal have undergone gene editing.

Another embodiment of the invention provides any of the CARs, nucleic acids, recombinant expression vectors, host cells, population of cells, or pharmaceutical compositions of the invention for use in the treatment or prevention of a condition in a mammal, wherein the condition is cancer. The cancer may be any of the cancers described herein with respect to other aspects of the invention.

The following examples further illustrate the invention but, of course, should not be construed as in any way limiting its scope.

EXAMPLES

The following materials and methods were employed in the experiments described in Examples 1-11.
Cell Lines and Primary Cells The CD30$^+$ target cells used in these experiments were the CD30$^+$ lymphoma cell lines SU-DHL-1 (lymphoma, American Type Culture Collection (ATCC)), HH (T-cell lymphoma, ATCC), and HDLM-2 (Hodgkin lymphoma, DSMZ). A leukemia cell line called bv173 (kind gift from Adrian Wiestner, NHLBI) was transduced with the gene for CD30 by using the gammaretroviral vector MSGV (Hughes et al., *Human Gene Ther.*, 16(4): 457-472 (2005)) to provide another CD30$^+$ target (CD30-bv173). The following CD30-negative cell lines were used: the leukemia cell line ngfr-bv173 (bv173 transduced with the low-affinity nerve growth factor gene by using the MSGV gammaretroviral vector), the T-cell leukemia cell line CCRF-CEM (ATCC), Saos-2 (a bone sarcoma cell line, ATCC); A549 (a lung carcinoma cell line, ATCC); MDA-MB231 (a breast cancer cell line, ATCC), 293GP (a human embryonic kidney cell line, kind gift of Steven Rosenberg, National Cancer Institute (NCI)), TC71 (a Ewings sarcoma cell line, kind gift of S.A. Rosenberg, NCI), COLO205 (a colon carcinoma cell line, NCI tumor repository), U251 (a glioblastoma cell line, NCI tumor repository) and Panc10.05 (a pancreatic carcinoma cell line, ATCC). Primary human CD34$^+$ hematopoietic stem cells from a patient were also used as targets. Tissue samples or peripheral blood mononuclear cells (PBMC) from patients enrolled on NCI IRB-approved clinical trials were used to initiate T-cell cultures.
Real-Time qPCR to Quantitate CD30 Transcript Copies CD30 cDNA copies in samples of cDNA from 48 human tissues included in the human normal quantitative polymerase chain reaction (qPCR) array (Origene, Rockville, Md.) were quantitated by performing qPCR with a CD30-specific primer and probe set (Invitrogen, Waltham, Mass.). As a positive control, CD30 cDNA copies in cDNA of the CD30$^+$ lymphoma cell line HH were quantitated. RNA was extracted from the plasmacytoma cells with an RNEASY mini kit (Qiagen, Venlo, Netherlands), and cDNA was synthesized with standard methods. A standard curve for the CD30 qPCR was created by amplifying dilutions of a plasmid that encoded the full-length cDNA of CD30 (Origene). The qPCR accurately detected copy numbers from 10 to $10^9$ copies of CD30 per reaction. The number of β-actin cDNA copies in the same tissues was also quantitated with a TAQMAN β-actin primer and probe kit (Applied Biosystems, Grand Island, N.Y.). A β-actin standard curve was created by amplifying serial dilutions of a β-actin plasmid. All qPCR reactions were carried out on a Roche LIGHTCYCLER480 machine. Data were expressed as CD30 cDNA copies/100,000 actin cDNA copies.
Construction of Anti-CD30 Chimeric Antigen Receptors (CARs)

Sequences of 4 anti-human CD30 antibodies were obtained from patents. The specific antibody sequences used were from the fully human 5F11 and 17G1 antibodies (U.S. Pat. No. 7,387,776), the AC10 murine antibody (U.S. Patent Application Publication No. 2005/0123536), and the humanized XmAb2513 antybody (U.S. Patent Application Publication No. 2012/0014943). The 5F11 and 17G1 antibodies were obtained by vaccinating HuMab mice that are transgenic for human immunoglobulin genes. Mice are transgenic for human immunoglobulin genes, so the mice generate fully-human antibodies. The cAC10 murine antibody was obtained by vaccinating mice with human CD30, and the XmAb2513 is a humanized version of cAC10. The heavy chain and light chain variable-region sequences of these antibodies were used to design single chain variable fragments (scFvs) with the following pattern: light chain variable region-linker-heavy chain variable region. The linker had the following amino acid sequence: GSTSGS-GKPGSGEGSTKG (SEQ ID NO: 10) (Kochenderfer et al., *J. Immunother.*, 32(7): 689-702 (2009)).

The first anti-CD30 CAR DNA designed was designated 5F11-CD8BBZ (SEQ ID NO: 18). The sequence of this CAR followed this pattern from the 5' end to the 3' end: CD8α leader sequence (SEQ ID NO: 9), 5F11 scFv (SEQ ID NO: 23), hinge and TM regions of the human CD8α molecule (SEQ ID NO: 11), the cytoplasmic portion of the 4-1BB (CD137) molecule (SEQ ID NO: 14), and the cytoplasmic portion of the CD3ζ molecule (SEQ ID NO: 15). Two versions of 5F11-CD8BBZ were synthesized. One version included a 4-1BB sequence containing a N-terminal RFVSS amino acid sequence (SEQ ID NO: 19); and the other version lacked the RFVSS sequence (SEQ ID NO: 19). The next CAR designed was identical to 5F11-CD8BBZ except that the scFv had variable regions from the 17G1 antibody. A series of CD28-containing CARs was next designed. 5F11-CD828Z (SEQ ID NO: 17) was designed by replacing the 4-1BB portion of 5F11-CD8BBZ with the cytoplasmic domain of the CD28 molecule (SEQ ID NO: 12). 5F11-28Z (SEQ ID NO: 16) was designed next. This CAR had the following pattern from the 5' to 3' end: CD8α leader sequence (SEQ ID NO: 9), 5F11 scFv (SEQ ID NO: 23), hinge and TM and cytoplasmic regions of the human CD28 molecule (SEQ ID NO: 13), and the cytoplasmic portion of the CD3ζ molecule (SEQ ID NO: 15). AC10-28Z and XmAb2513-28Z were constructed by replacing the 5F11 scFv of 5F11-28Z with the AC10 or XmAb2513 scFvs, respectively.

A negative-control CAR that contained the SP6 scFv that recognized the hapten 2,4,6-trinitrophenyl was also constructed (Eshhar et al., *PNAS*, 90(2):720-724 (1993)). This CAR was referred to as SP6-CD828Z. The SP6 CAR has been previously reported and contained the CD8α hinge and TM regions, the cytoplasmic portion of CD28 and the signaling domains of the CD3ζ molecule (Carpenter et al., *Clin. Cancer Res.*, 19(8): 2048-2060 (2013)). The SP6-CD828Z CAR does not recognize murine or human proteins and was used as a negative control.

DNA encoding all of the CAR sequences was codon optimized (co) and synthesized by Invitrogen (GeneArt) with appropriate restriction sites. The CAR sequences were ligated into a lentiviral vector plasmid designated pRRLSIN.cPPT.MSCV.coDMF5.oPRE (Yang et al., *J. Immunother.*, 33(6): 648-658 (2010)). The coDMF5 portion of this vector was replaced with the CAR sequences by using standard restriction enzyme and ligation methods.

Lentiviral Supernatant Production

Supernatant that contained lentiviruses encoding each CAR was produced by following a slightly modified version of a previously published protocol (Yang et al., *J. Immunother.*, 33(6): 648-658 (2010)). To produce the supernatant, 293T-17 cells (ATCC) were transfected with the following plasmids as detailed previously: pMD2.G (encoding the vesicular stomatitis virus envelope), pMDLg/pRRE (encoding gag and pol), pRSV-Rev (encoding Rev), and the appropriate CAR-encoding plasmid (Yang et al., *J. Immunother.*, 33(6): 648-658 (2010)). After transfection, the transfected 293T-17 cells were cultured for approximately 40 hours. The culture supernatant was then collected and centrifuged to remove cell debris. Then the supernatant was ultrafiltered by using AMICON Ultra-15 ultrafilter units from Merk Millipore Ltd. (Billerica, Mass.).

T Cell Transductions

T cells were cultured in a similar manner as described previously (Kochenderfer et al., *J. Immunother.*, 32(7): 689-702 (2009)). In brief, PBMC were stimulated with the anti-CD3 monoclonal antibody OKT3 (Ortho, Rochester, N.Y.) in AIM V medium (Invitrogen) containing 5% human AB serum (Valley Biomedical, Winchester, Va.) and 300 international units (IU)/mL of interleukin-2 (IL-2, Chiron (Emeryville, Calif.)). Twenty-two to twenty-six hours after the cultures were started, the activated PBMC were counted and centrifuged. After the cells were centrifuged, the culture media was removed from the pelleted cells and saved. The cells were re-suspended (at $1 \times 10^6$ cells/mL) in the same media in which the cultures were initiated, and lentiviral vector was added to the media along with protamine sulfate. The cells were cultured in 6-well tissue culture plates (Corning, Corning, N.Y.) with $4 \times 10^6$ T cells/well. The cells were then cultured for approximately 48 hours at 37° C. The cells were then centrifuged, decanted, and resuspended at $0.5 \times 10^6$/mL in fresh AIM V media$^+$5% human AB serum$^+$ 300 IU/mL IL-2 for culture. The cell concentration was adjusted to $0.5 \times 10^6$ T cells/mL every 2 to 3 days.

CAR Detection on Transduced T Cells by Protein L Staining

Cells were washed and suspended in fluorescence-activated cell sorting (FACs) buffer (phosphate-buffered saline (PBS) plus 0.1% sodium azide and 0.4% bovine serum albumin (BSA)). Biotin-labeled protein L (GenScript, Piscataway, N.J.) was added to detect the cell surface CAR scFvs. The cells were incubated at 4° C. for 30 minutes and washed twice. The cells were suspended in FACs buffer and blocked with normal mouse IgG (Invitrogen). The cells were then stained with phycoerythrin (PE)-labeled streptavidin (BD Pharmingen, San Jose, Calif.), anti-CD4 (eBioscience, San Diego, Calif.), anti-CD8 (eBioscience), anti-CD30 (BD Pharmingen) and anti-CD3 (eBioscience). Flow cytometry acquisition was performed with a LSR II flow cytometer (BD Biosciences, Franklin Lakes, N.J.), and analysis was performed with FLOWJO software (Treestar, Inc. Ashland, Oreg.). The percentage of CAR-expressing (CAR$^+$) T cells was calculated as the percentage of T cells in CAR-transduced cultures that stained with protein L minus the percentage of identically-cultured untransduced T cells from the same donor that stained with protein L in each experiment. T cells were stained for CD30 by using standard methods with an anti-CD30 antibody from BD Biosciences.

Interferon-γ ELISA

CD30$^+$ or CD30-negative target cells were combined with CAR-transduced T cells in duplicate wells of a 96-well round bottom plate in AIM-V medium$^+$5% human serum. The plates were incubated at 37° C. for 18-20 hours. Following the incubation, ELISAs for IFNγ were performed by using standard methods (Pierce, Waltham, Mass.).

CD107a Assay

For each T cell culture that was tested, two tubes were prepared. One tube contained CD30$^+$ target cells, and the other tube contained CD30-negative target cells. Both tubes contained CAR-transduced T cells, 1 ml of AIM-V medium$^+$ 5% human AB serum, a titrated concentration of an anti-CD107a antibody (eBioscience, clone eBioH4A3), and 1 μL of GOLGISTOP protein transport inhibitor (monesin, BD Biosciences). All tubes were incubated at 37° C. for 4 hours and then stained for CD3, CD4, and CD8.

Proliferation Assays

Cultures were set up in 24-well plates. Target cells included in cultures were either $0.5 \times 10^6$ irradiated CD30$^+$ cells or $0.5 \times 10^6$ irradiated CD30-negative cells. The cultures also included $0.75 \times 10^6$ T cells from cultures that expressed an anti-CD30 CAR. The T cells were labeled with carboxyfluorescein diacetate succinimidyl ester (CFSE, Invitrogen) as previously described (Mannering et al., *J. Immunol. Methods*, 283(1-2): 173-183 (2003)). The medium used in the cultures was AIM V$^+$5% human AB serum. IL-2 was not added to the medium. Four days after initiation, the live cells in each culture were counted with trypan blue for dead cell exclusion, and flow cytometry was performed as described under "CAR detection on transduced T cells by protein L staining."

Cytotoxicity Assay

Cytotoxicity assays were conducted as previously described (Kochenderfer et al., *J. Immunother.*, 32(7): 689-702 (2009)). Cytotoxicity was measured by comparing survival of CD30$^+$ HH lymphoma cells relative to the survival of negative-control CCRF-CEM cells. Both of these cell types were combined in the same tubes with CAR-transduced T cells. CCRF-CEM negative control cells were labeled with the fluorescent dye 5-(and-6)-(((4-chloromethyl)benzoyl)amino) tetramethylrhodamine (CMTMR) (Invitrogen), and CD30$^+$ HH lymphoma target cells were labeled with CFSE. T cell target cell cultures were set up in sterile 5 mL test tubes (BD) in duplicate at multiple T cell to target cell ratios. The target cells contained in the tubes were 50,000 CD30$^+$ HH cells along with 50,000 CCRF-CEM negative-control cells. The cultures were incubated for 4 hours at 37° C. Immediately after the incubation, 7AAD (7-amino-actinomycin D) (BD) was added, and flow cytometry acquisition was performed. For each T cell plus target-cell culture, the percent survival of CD30$^+$ HH target cells was determined by dividing the percent live HH cells by the percent live CCRF-CEM negative control cells. The corrected percent survival of HH target cells was calculated by dividing the percent survival of HH target cells in each T cell plus target cell culture by the ratio of the percent live HH target cells to percent live CCRF-CEM negative-control cells in tubes containing only HH target cells and CCRF-CEM cells without effector T cells. This correction was necessary to account for variation in the starting cell numbers and for spontaneous target cell death. Cytotoxicity was calculated as follows: the percent cytotoxicity of CD30$^+$ HH target cells=100-corrected percent survival of CD30$^+$ HH target cells.

Example 1

This example demonstrates that CD30 RNA was absent or expressed at very low levels in normal human tissues.

An analysis of CD30 expression was performed by qPCR on a panel of cDNA samples that were prepared from the RNA of 48 normal human tissues (FIGS. 1A and 1B). The results showed that CD30 was absent or expressed at very low levels in normal human tissues. These qPCR results were in agreement with extensive prior immunohistochemistry work performed by other investigators (Schwarting et al., *Blood*, 74(5): 1678-1689 (1989); Ito et al., *American J. Pathol.*, 145(2): 276-280 (1994); Falini et al., *Blood*, 85(1): 1-14 (1995)). Notably, the few organs that had low levels of CD30 RNA expression detected by qPCR were negative for CD30 by immununohistochemistry in experiments performed by other investigators (Schwarting et al., *Blood*, 74(5): 1678-1689 (1989); Ito et al., *American J. Pathol.*, 145(2): 276-280 (1994); Falini et al., *Blood*, 85(1): 1-14 (1995)). This prior immunohistochemistry work showed that CD30 was not expressed on the cells of major human organs except for decidual cells of the pregnant uterus (Ito et al., *American J. Pathol.*, 145(2): 276-280 (1994)).

Example 2

This example demonstrates the presence or absence of CD30 expression on the surface of cell lines, primary human CDD34$^+$ cells, and primary human peripheral blood mononuclear cells.

Other investigators have detected CD30 on the surface of several different types of lymphoma including Hodgkin lymphoma, anaplastic large cell lymphoma, some B-cell lymphomas, and several types of T-cell lymphomas (Stein et al., *Blood*, 66(4): 848-858 (1985); Schwarting et al., *Blood*, 74(5): 1678-1689 (1989); Falini et al., *Blood*, 85(1): 1-14 (1995)). CD30 expression was assayed on the surface of a series of cell lines by flow cytometry. It was found that some cell lines, such as the HH lymphoma cell line, expressed high levels of CD30. Some other cell lines, such as the COL0205 cell line, did not express CD30. The ngfr-bv173 cell line did not express CD30. The CD30-bv173 cell line (which was transduced to express CD30) did express CD30. CD30 expression was also assessed on primary human CDD34$^+$ cells and primary human peripheral blood mononuclear cells; neither the CD34$^+$ cells nor the PBMC expressed CD30.

Example 3

This example demonstrates the T-cell surface expression of CARs, each CAR incorporating one of the scFvs derived from the 5F11, AC10, and the XmAb2513 antibodies.

CARs were generated incorporating one of each of 4 different anti-CD30 single-chain variable fragments (scFvs). These scFvs were derived from 4 different monoclonal antibodies, 17G1, 5F11, AC10, and XmAb2513. A CAR incorporating the 17G1-derived scFv was not expressed at high levels on T cells and was not studied extensively. CARs incorporating scFvs derived from one of each of the 5F11, AC10, and the XmAb2513 antibodies were studied extensively in vitro. To evaluate the different scFvs, a CAR design with hinge, TM and cytoplasmic regions from the CD28 costimulatory molecule and a CD3ζ T-cell activation molecule at the C-terminus was used.

First, T-cell surface expression of CARs incorporating scFvs from one of each of the 5F11, AC10, and XmAb2513 antibodies was compared by flow cytometry. Human T cells were stimulated with the anti-CD3 antibody OKT3 on day 0. T cells were tranduced with lentiviruses encoding either 5F11-28Z, AC10-28Z, or XmAb2513-28Z on day 1. As a control, some T cells were left untransduced. The T cells proliferated in IL-2-containing media. On day 7, the cells were stained with protein L, CD3, CD4, CD8, and CD30 and analyzed by flow cytometry. All three CARs were expressed at high levels on T cells, and the levels of surface expression of the 3 different CARs were nearly identical. The percentages of cells expressing CD8 and the CAR are shown in Table A. Plots were gated on live CD3$^+$ lymphocytes. Similar results were obtained with cells from 2 different patients.

TABLE A

| | | CD8$^+$CAR$^+$ | CD8$^-$CAR$^-$ | CD8$^+$CAR$^-$ | CD8$^-$CAR$^+$ |
|---|---|---|---|---|---|
| Cells | 5F11-28Z | 80.70 | 1.04 | 2.42 | 15.80 |
| transduced | AC10-28Z | 61.90 | 1.02 | 3.60 | 33.50 |
| with CAR | XmAb2513-28Z | 64.70 | 1.16 | 3.50 | 30.60 |
| Control | Untransduced | 1.44 | 30.70 | 66.30 | 1.48 |

Example 4

This example demonstrates that T cells expressing the 5F11-28Z CAR are functionally superior to T cells expressing either the AC10-28Z CAR or the XmAb2513 CAR.

The percentage of total T cells that expressed CD30 was evaluated because activated T cells express CD30 (Horie et al., *Seminars in immunology*, 10(6): 457-470 (1998)), so elimination of CD30+ T cells could possibly occur in cultures of anti-CD30-CAR-expressing T cells. The percentage of total T cells that expressed CD30 was evaluated with the same T-cell cultures used to evaluate CAR expression in Example 3.

It was found that CD30+ T cells were greatly reduced in cultures of 5F11-28Z-transduced T cells compared to cultures of AC10-28Z-transduced T cells, XmAb2513-28Z-transduced T cells, and untransduced T cells. The percentages of cells expressing CD8 and CD30 are shown in Table B. Plots were gated on live CD3+ lymphocytes. Table B shows that the percentage of cells expressing CD30 was much lower among the T cells that were transduced with the gene for 5F11-28Z compared to untransduced T cells or T cells transduced with the genes encoding AC10-28Z or XmAb-28Z. Similar results were obtained in 6 experiments. These results suggested that 5F11-28Z-transduced T cells were more effective than AC10-28Z-transduced T cells or XmAb2513-28Z-transduced T cells at eliminating CD30+ T cells from the cultures.

TABLE B

|  |  | $CD8^+CD30^+$ | $CD8^-CD30^-$ | $CD8^+CD30^-$ | $CD8^-CD30^+$ |
|---|---|---|---|---|---|
| Cells transduced with CAR | 5F11-28Z | 2.65 | 15.30 | 81.40 | 0.63 |
|  | AC10-28Z | 27.70 | 16.90 | 39.00 | 16.40 |
|  | XmAb2513-28Z | 30.80 | 13.70 | 38.90 | 16.60 |
| Control | Untransduced | 10.50 | 19.60 | 57.50 | 12.40 |

Cells from the same cultures evaluated in the experiments of Example 2 and Table A were assessed for degranulation. T cells were cultured with the CD30+ target cell SUDHL-1 for 4 hours. The CD107a molecule is a marker of T-cell degranulation. An antibody against CD107a was included in the cultures to detect degranulation. Cells were also stained for CD3 and CD8. The plots were gated on live CD3+ lymphocytes.

Table C shows the percentages of cells expressing CD8 and CD107a. Greater CD30-specific degranulation was demonstrated by 5F11-28Z-transduced T cells compared to either AC10-28Z or XmAb2513-28Z-transduced cells, as shown in Table C. Similar results were obtained with cells from 2 different donors.

TABLE C

|  |  | $CD8^+CD107a^+$ | $CD8^-CD107a^-$ | $CD8^+CD107a^-$ | $CD8^-CD107a^+$ |
|---|---|---|---|---|---|
| Cells transduced with CAR | 5F11-28Z | 47.40 | 11.50 | 36.70 | 4.32 |
|  | AC10-28Z | 6.18 | 35.00 | 57.40 | 1.34 |
|  | XmAb2513-28Z | 7.72 | 29.80 | 60.60 | 1.86 |
| Control | Untransduced | 0.62 | 29.80 | 68.30 | 1.32 |

CD30-specific interferon-gamma (IFNγ) release upon coculture with target cells was measured in an enzyme-linked immunosorbant assay (ELISA). 5F11-28Z-transduced T cells demonstrated greater CD30-specific IFNγ release as compared to either AC10-28Z or XmAb2513-28Z-transduced cells (Table D-1). SUDHL-1, HH, and CD30-bv173 in Table D-1 are CD30+ cell lines. NGFR-bv173 and CCRF-CEM in Table D-1 are CD30-negative cell lines. The values in Table D-1 are pg/mL of IFNγ released at the end of the culture period. The percentage of T cells expressing each CAR (Table D-2) was determined by staining CAR-transduced and untransduced T cells with Protein L and subtracting the % protein L staining of untransduced T cells from the % protein L staining of each CAR-transduced T-cell population.

These results confirmed that T cells expressing 5F11-28Z were functionally superior to T cells expressing either AC10-28Z or XmAb2513.

TABLE D-1

|  | Targets |  |  |  |  |  |
|---|---|---|---|---|---|---|
| CAR expressed by T cells | SUDHL-1 | HH | CD30-bv173 | NGFR-bv173 | CEM | T cells alone (control) |
| 5F11-28Z | 25468 | 78624 | 3781 | 33 | 31 | 13 |
| AC10-28Z | 4849 | 8136 | 538 | 14 | 12 | <12 |
| XmAb2513-28Z | 2444 | 4699 | 388 | 13 | 12 | <12 |
| Untransduced | 17 | 29 | 39 | 26 | 16 | <12 |

TABLE D-2

| CAR expressed by T cells | % T cells expressing CAR |
|---|---|
| 5F11-28Z | 93.6 |
| AC10-28Z | 92.5 |
| XmAb2513-28Z | 92.3 |
| Untransduced | 0 |

Example 5

This example demonstrates the CD30-specific function of the 5F11-28Z and 5F11-CD828Z CARs.

Figure 2:
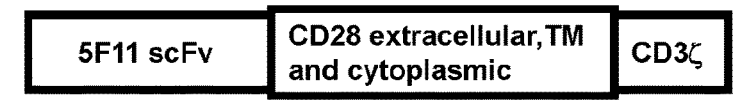
FIGS. 2A-2C are schematics illustrating the structures of the 5F11-28Z (A), 5F11-CD828Z (B), and 5F11-CD8BBZ (C) CARs, respectively.
Figure 2:
Figure 2:

Because of the functional superiority of T cells containing the 5F11 scFv, further experiments were carried out with this CAR. Three CARs containing the 5F11 scFv were designed (FIGS. 2A-2C). The CD30-specific function of 5F11-28Z and 5F11-CD828Z was confirmed in an IFNγ ELISA assay (Table E-1). T cells expressing the CAR were cultured with the target cells in Table E-1 overnight, and then an IFNγ ELISA was performed. SUDHL-1 and HDLM-2 in Table E-1 are CD30+ cell lines. NGFR-bv173, CCRF-CEM, and 293GP in Table E-1 are CD30-negative cell lines. The values in Table E-1 are pg/mL of IFNγ released at the end of the culture period. The percentage of T cells expressing each CAR was determined by staining CAR-transduced and untransduced T cells with Protein L and subtracting the % protein L staining of untransduced T cells from the % protein L staining of each CAR-transduced T-cell population (Table E-2).

TABLE E-1

| CAR expressed by T cells | Targets | | | | | T cells alone (control) |
|---|---|---|---|---|---|---|
| | SUDHL-1 | HDLM-2 | NGFR-bv173 | CCRF-CEM | 293GP | |
| 5F11-28Z | 3489 | 3534 | 14 | 23 | 176 | <12 |
| 5F11-CD828Z | 2296 | 3009 | <12 | <12 | 100 | <12 |

TABLE E-1-continued

| CAR expressed by T cells | Targets | | | | | T cells alone (control) |
|---|---|---|---|---|---|---|
| | SUDHL-1 | HDLM-2 | NGFR-bv173 | CCRF-CEM | 293GP | |
| Untransduced | 13 | 20 | 30 | <12 | 137 | <12 |

TABLE E-2

| CAR expressed by T cells | % T cells expressing CAR |
|---|---|
| 5F11-28Z | 95.8 |
| 5F11-CD828Z | 97.1 |
| Untransduced | 0 |

Example 6

This example demonstrates that the 5F11-28Z and 5F11-CD828Z CARs provide superior CD30-specific activity as compared to the 5F11-CD8BBZ CAR.

T cells were transduced with one of three different CARs, 5F11-28Z, 5F11-CD828Z, or 5F11-CD8BBZ. The CAR-transduced T cells were cultured with either the CD30+ target cell CD30-bv173 or the CD30-negative cell line ngfr-bv173 for 4 hours. An antibody against CD107a was included in the cultures to detect degranulation. Cells were also stained for CD3 and CD8. The plots were gated on live CD3+ lymphocytes.

Compared to the 4-1BB-containing CAR 5F11-CD8BBZ, the CD28-containing CARs 5F11-28Z and 5F11-CD828Z degranulated to a greater extent against CD30+ target cells; in addition, compared to 5F11-CD8BBZ, the CD28-containing CARs had less background degranulation against CD30-negative targets (Tables F-1 and F-2). Table F-1 shows the percentages of cells expressing CD8 and CD107a upon co-culture with the CD30+ target cell CD30-bv173. Table F-2 shows the percentages of cells expressing CD8 and CD107a upon co-culture with the CD30-negative cell line ngfr-bv173. Similar results were seen in 2 different donors. Cell surface CAR expression of the T cells used in this experiment were: 5F11-28Z, 95.8%; 5F11-CD828Z, 96.0%; 5F11-CD8BBZ, 93.2%.

TABLE F-1

| | | CD30-bv173 targets | | | |
|---|---|---|---|---|---|
| | | CD8+CD107a+ | CD8−CD107a− | CD8+CD107a− | CD8−CD107a+ |
| CAR | 5F11-28Z | 39.50 | 13.60 | 40.10 | 6.82 |
| | 5F11-CD828Z | 30.00 | 23.30 | 35.20 | 11.60 |
| | 5F11-CD8BBZ | 25.90 | 21.60 | 40.40 | 12.10 |
| Control | Untransduced | 1.40 | 27.10 | 70.20 | 1.29 |

TABLE F-2

| | | Ngfr-bv173 targets | | | |
|---|---|---|---|---|---|
| | | CD8+CD107a+ | CD8−CD107a− | CD8+CD107a− | CD8−CD107a+ |
| CAR | 5F11-28Z | 3.54 | 16.80 | 78.60 | 1.01 |
| | 5F11-CD828Z | 3.90 | 31.10 | 62.50 | 2.49 |
| | 5F11-CD8BBZ | 6.66 | 27.00 | 61.30 | 5.05 |
| Control | Untransduced | 1.53 | 26.40 | 70.70 | 1.35 |

Similarly, when antigen-specific IFNγ production was evaluated, T cells expressing the 5F11-28Z CAR produced the most IFNγ when cultured with CD30+ target cells. When compared to T cells expressing a CAR containing a 4-1BB moiety, T cells expressing either 5F11-28Z or 5F11-CD828Z exhibited less background IFNγ production against CD30-negative targets (Table G). HH in Table G is a CD30+ lymphoma cell line. A549, TC71, So18, Panc10.05, and MDA231 in Table G are CD30-negative cells lines. Primary CD34+ hematopoietic stem cells were also included (Table G). 95.8% of the 5F11-28Z T cells in Table G expressed the CAR as measured by flow cytometry.

TABLE G

| | 5F11-28Z | 5F11-CD828Z | 5F11-CD8BBZ | Untransduced |
|---|---|---|---|---|
| HH | 126692 | 34289 | 47746 | 508 |
| A549 | 107 | 66 | 2491 | 20 |

TABLE G-continued

|  | 5F11-28Z | 5F11-CD828Z | 5F11-CD8BBZ | Untransduced |
|---|---|---|---|---|
| TC71 | 773 | 97 | 1724 | 28 |
| Sol8 | 92 | 89 | 2357 | 33 |
| Panc10.05 | 48 | 63 | 2526 | 12 |
| MDA231 | 354 | 107 | 1498 | 163 |
| Primary CD34+ | 153 | 70 | 1389 | 71 |
| T cells alone | 26 | 68 | 1405 | <12 |

Because the CD30-specific activity of CD28-containing CARs was superior to the CD30-specific activity of the 4-1BB-containing CAR, it was concluded that 5F11-28Z and 5F11-CD828Z were the most promising CARs for further development. Compared to T cells expressing 5F11-CD828Z or 5F11-CD8BBZ, T cells expressing the 5F11-28Z CAR exhibited the strongest recognition of CD30+ target cells when all of the experiments were analyzed (Tables D-1, D-2, E-1, E-2, and G).

Example 7

This example demonstrates that T cells expressing the 5F11-28Z CAR proliferate in a CD30-specific manner in vitro.

Figure 3:
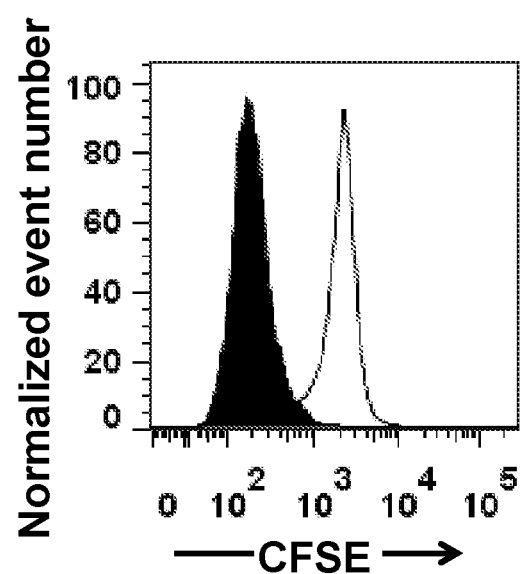
FIG. 3 is a histogram showing the extent of dilution of the fluorescent dye CFSE when CFSE-labeled T cells expressing 5F11-28Z were cultured with CD30-bv173 cells (CD30+, filled black histogram) or negative control NGFR-bv173 cells (CD30-negative, open histogram).

T cells expressing 5F11-28Z were labeled with the fluorescent dye CFSE, which is diluted as cells proliferate. As shown in FIG. 3, CFSE diluted to a greater extent when 5F11-28Z T cells were cultured with CD30-bv173 cells (CD30+, filled black histogram) than when 5F11-28Z-transduced T cells were cultured with negative control NGFR-bv173 cells (CD30-negative, open histogram). Accordingly, T cells expressing the 5F11-28Z CAR proliferated in a CD30-specific manner in vitro (FIG. 3). Plots were gated on live, CD3+, CAR-expressing lymphocytes. Similar results were obtained in 4 different experiments.

Example 8

This example demonstrates that the number of anti-CD30-CAR-transduced T cells in cultures expands sufficiently to yield sufficient cells for clinical adoptive cell transfer.

Activated T cells express CD30, and T-cell cultures containing T cells expressing anti-CD30 CARs had reduced numbers of CD30+ T cells compared to cultures of untransduced T cells. This reduced number of CD30+ T cells in cultures of anti-CD30-CAR-transduced T cell cultures was likely due to elimination of CD30+ T cells by the CAR-expressing T cells. It was sought to determine whether or not anti-CD30-CAR-transduced T cells could proliferate and survive sufficiently to generate the $10^8$ to $10^9$ T cells normally administered in clinical trials of CAR T-cell therapies.

Figure 4:
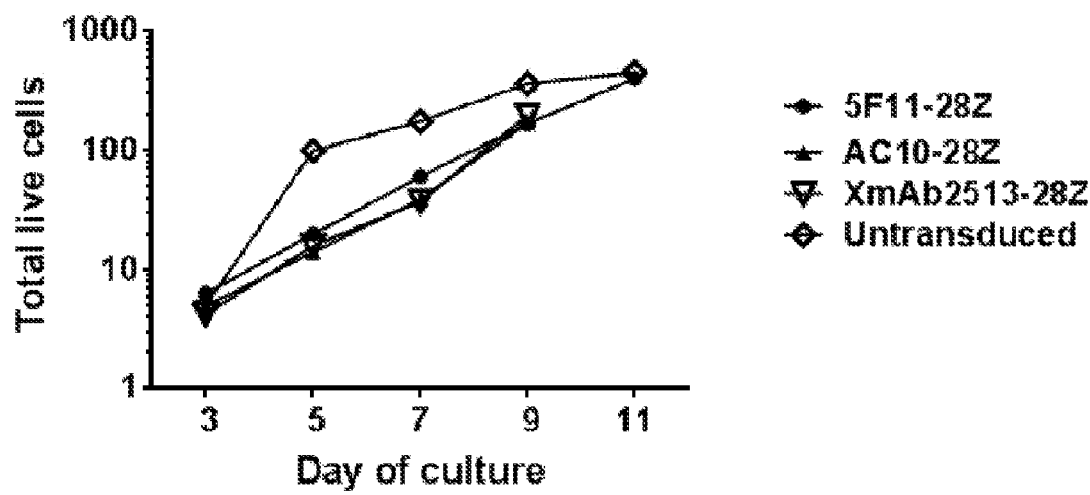
FIG. 4A is a graph showing the number of total live cells from a first donor at various time points (days) of culture, wherein the T cells were untransduced (open squares) or transduced with 5F11-28Z (circles), AC10-28Z (▲), or XmAb2513-28Z (open triangles).
FIG. 4B is a graph showing the number of total live cells from a second donor at various time points (days) of culture, wherein the T cells were untransduced (diamonds) or transduced with 5F11-28Z (circles), AC10-28Z (▲), or XmAb2513-28Z (open triangles).
Figure 4:
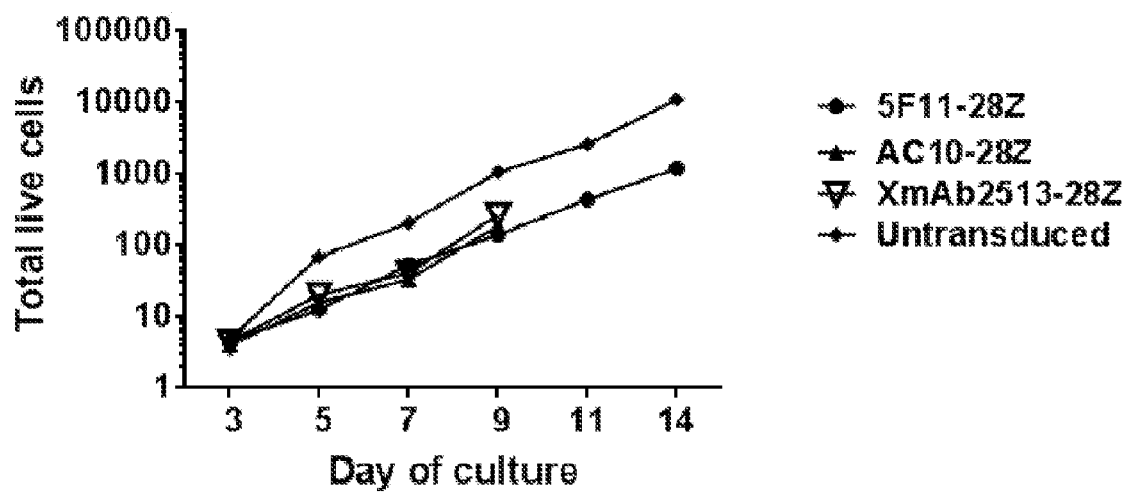

T-cell cultures were initiated with OKT3 stimulation on day 0. T cells were left untransduced or transduced on day 1 of culture with the 5F11-28Z, AC10-28Z, or XmAb2513-28z and allowed to proliferate in vitro in IL-2-containing media. Total live cells were counted by light microscopy with trypan blue. For all 3 of the CARs, greater than 90% of T cells that were transduced with each CAR expressed the CAR on the T-cell surface as detected by protein L staining. The results with cells from two different donors are shown in FIGS. 4A and 4B, respectively. The AC10-28Z and XmAb2513-28Z CAR T cell cultures were intentionally stopped on day 9 of culture, and the 5F11-28Z-transduced and untransduced cultures were intentionally stopped on day 11.

Figure 5:
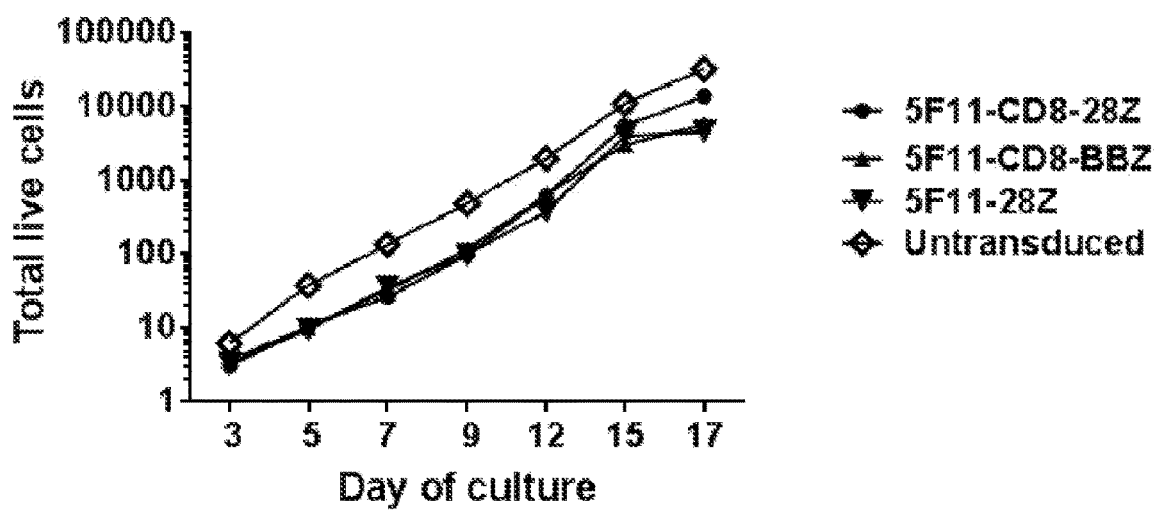
FIGS. 5A and 5B are graphs showing the number of total live cells from a first (A) and second (B) donor at various time points (days) of culture, wherein the T cells were untransduced (open squares) or transduced with 5F11-28Z (▼), 5F11-CD8BBZ (▲), or 5F11-CD8-28Z (circles).
Figure 5:
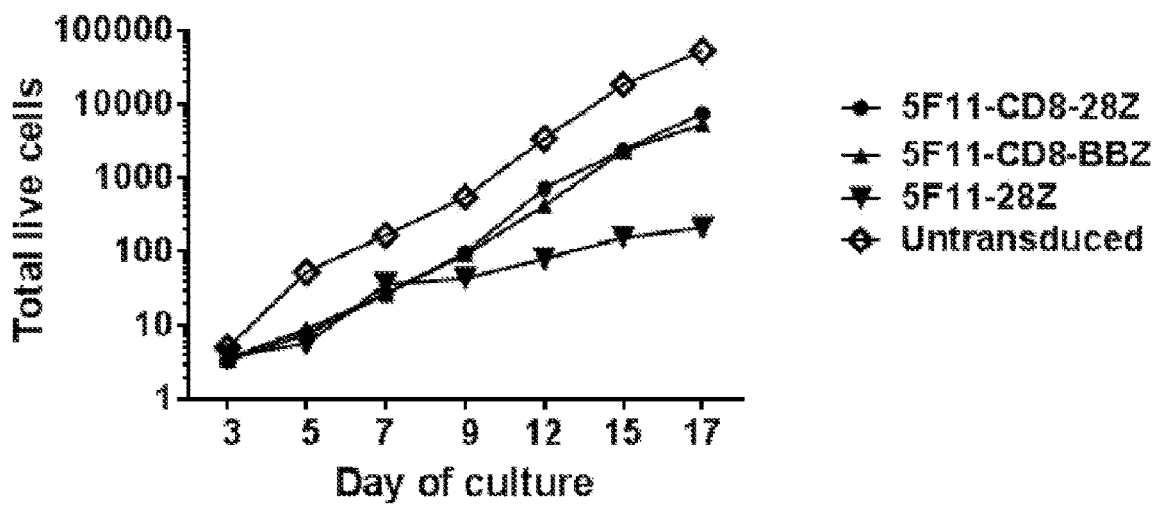

In a separate experiment, T-cell cultures were initiated with OKT3 stimulation on day 0. T cells were left untransduced or transduced with 5F11-CD8-28Z, 5F11-CD8-BBZ, or 5F11-28Z and allowed to proliferate in vitro in IL-2-containing media. Total live cells were counted by light microscopy with trypan blue. For all 3 of the CARs, greater than 90% of T cells that were transduced with each CAR expressed the CAR on the T-cell surface as detected by protein L staining. The results from two different donors are shown in FIGS. 5A and 5B, respectively.

In repeated experiments, it was shown that the number of anti-CD30-CAR-transduced T cells in cultures did expand sufficiently to yield sufficient cells for clinical adoptive cell transfer (FIGS. 4A-4B and 5A-5B).

Example 9

This example demonstrates that 5F11-28Z-transduced T cells can kill CD30+ HH lymphoma cells in vitro.

Figure 6:
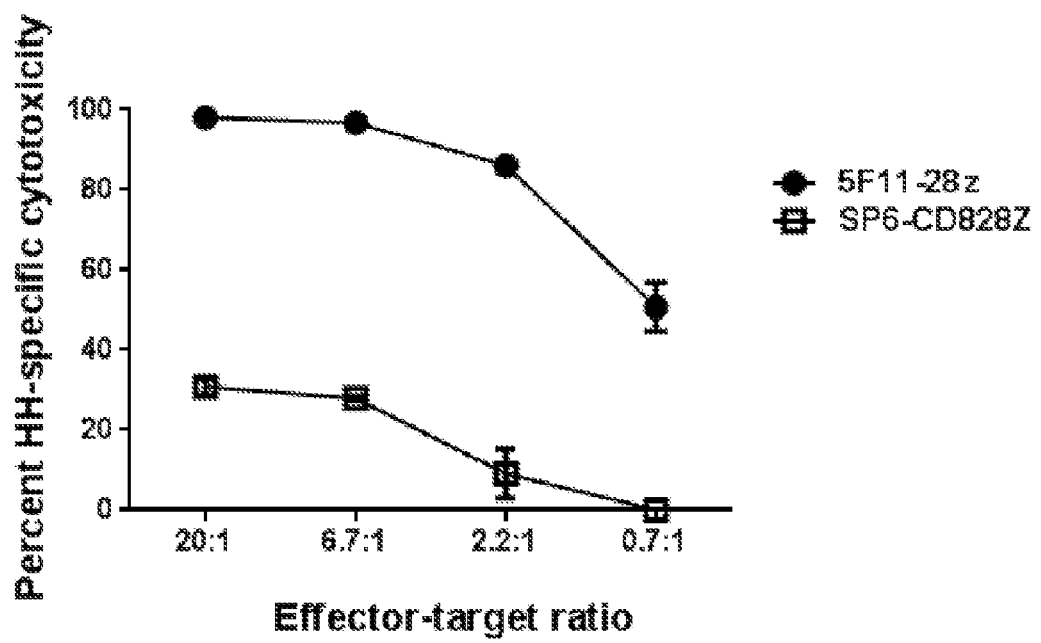
FIG. 6 is a graph showing the percent HH-specific cytotoxicity measured following co-culture of T cells transduced with the 5F11-28Z CAR (effector) (circles) with HH lymphoma cells (target) at various effector:target ratios. The data are presented as the percent cytotoxicity of HH cells relative to the percent cytotoxicity of the CD30-negative target cell CCRF-CEM. T cells expressing the SP6-CD828Z CAR (squares) were used as a negative control (effector).

An in vitro flow cytometry cytotoxicity assay was performed that showed that 5F11-28Z-expressing T cells can specifically kill CD30+ HH lymphoma cell line cells. The assay had a 4-hour incubation period. As shown in FIG. 6, it was established that 5F11-28Z-transduced T cells could kill CD30+ HH lymphoma cells in vitro.

Example 10

This example demonstrates the ability of T cells expressing 5F11-28Z and 5F11-CD828Z to eradicate tumors in vivo. This example also demonstrates that tumor-bearing mice treated with T cells expressing 5F11-28Z and 5F11-CD828Z survive long-term with no tumor recurrence.

The ability of T cells expressing 5F11-28Z and 5F11-CD828Z to eradicate tumors in vivo was assessed. Subcutaneous tumors of CD30+ HH lymphoma cells were established in immunocompromised nod scid common-gamma-chain-deficient (NSG) mice. Four days later, the mice were treated with a single intravenous infusion of $8 \times 10^6$ T cells from the same donor that were transduced with either 5F11-28Z or 5F11-CD828Z or SP6-CD828Z. A fourth group of mice was left untreated. SP6-CD828Z is a CAR that does not recognize human or murine proteins. SP6-CD828Z was used as a negative control. Each group contained 10 mice except the untreated group that contained 9 mice. Each experiment used T cells from a different normal donor.

Figure 7:
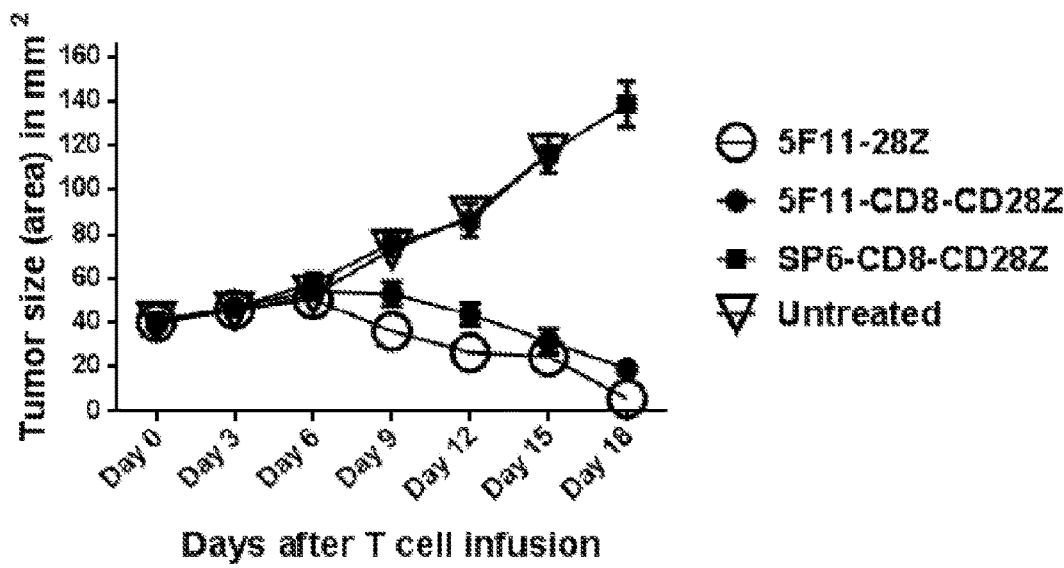
FIG. 7A is a graph showing the tumor size (area) ($mm^2$) of mice that were untreated (open triangle) or treated with an intravenous infusion of 8 million T cells that were transduced with either 5F11-28Z (open circles), 5F11-CD828Z (closed circles), or SP6-CD828Z (squares) at various time points (days) after T cell infusion. The results shown are the combined results of 2 experiments. Results are reported as tumor size with standard error of the mean.
FIG. 7B is a graph showing the percent survival of tumor-bearing mice that were untreated (open triangle) or treated with an intravenous infusion of 8 million T cells that were transduced with either 5F11-28Z (open circles), 5F11-CD828Z (closed circles), or SP6-CD828Z (squares) at various time points (days) after T cell infusion.
Figure 7:
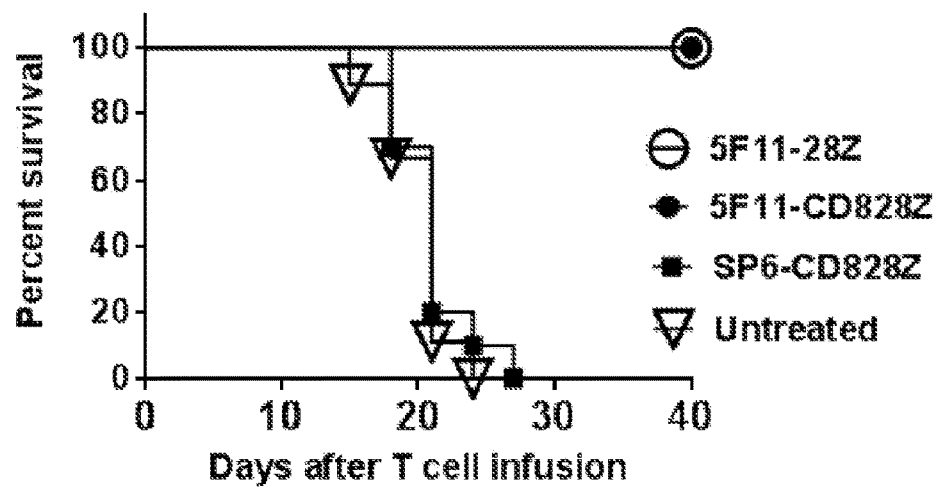
Figure 8:
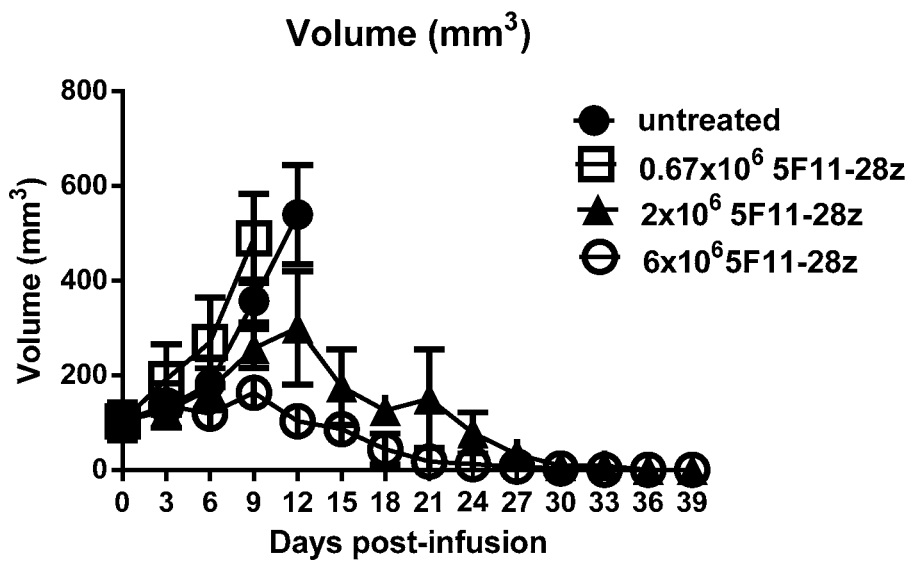
FIG. 8A is a graph showing the tumor volume ($mm^2$) in mice that were untreated (closed circle) or treated with a single infusion of $0.67 \times 10^6$ (squares), $2 \times 10^6$ (triangles), or $6 \times 10^6$ (circles) T cells transduced with 5F11-CD28Z at various time points (days) after T cell infusion.
FIG. 8B is a graph showing the percent survival of tumor-bearing mice that were untreated (closed circle) or treated with a single infusion of $0.67 \times 10^6$ (squares), $2 \times 10^6$ (triangles), or $6 \times 10^6$ (circles) T cells transduced with 5F11-CD28Z at various time points (days) after T cell infusion.
Figure 8:
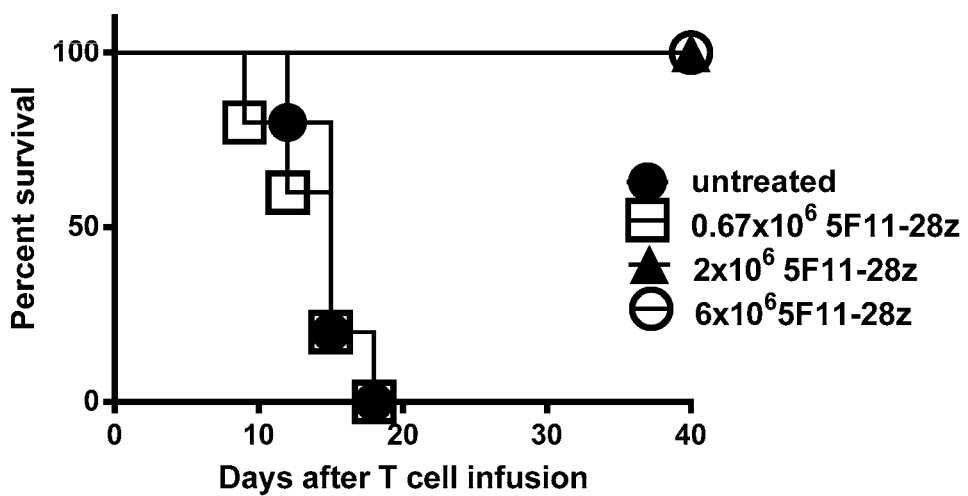

The results are shown in FIGS. 7A and 7B. Tumors were completely eradicated in the mice receiving T cells expressing 5F11-28Z or 5F11-CD828Z; in contrast, progressive tumor growth occurred in the mice receiving SP6-CD828Z-transduced T cells and the untreated mice (FIG. 7A). Similarly, mice receiving T cells that were transduced with 5F11-28Z or 5F11-CD828Z all survived long-term with no tumor recurrence; in contrast, untreated mice and mice receiving SP6-CD828Z-transduced T cells all died with progressive tumors (FIG. 7B). Survival fractions were calculated by the Kaplan-Meier method.

Example 11

This example demonstrates that the anti-CD30 CARs are effective at eradicating tumors despite the presence of soluble CD30.

CD30 is shed by CD30+ malignant cells in some patients with CD30+ lymphomas (Visco et al., *European J. Haematol.*, 77(5): 387-394 (2006); Pizzolo et al., *British J. Haematol.*, 75(2): 282-284 (1990)). Therefore, the impact of soluble CD30 on the ability of anti-CD30 CARs to recognize target cells was assessed. T cells that were untransduced or transduced to express the 5F11-28Z CAR were cultured with the target cells indicated in Table H overnight, and then a standard IFNγ ELISA was performed. The HH cells in Table H are CD30+ cell lines. The numbers in Table H followed by µg/mL (leftmost column of Table H) refer to the concentration of human CD30 protein added to the media during the entire time that the T cells and target cells were cultured together. U251 and Colo-205 in Table H are CD30-negative cell lines. The numbers in the rightmost two columns of Table H are pg/mL of IFNγ released at the end of the culture period. 94.8% of the 5F11-28Z T cells in Table H expressed the CAR as measured by flow cytometry.

TABLE H

| Targets | 5F11-28Z-transduced | Untransduced |
| --- | --- | --- |
| HH 0 µg/mL CD30 | 23021 | Not determined |
| HH 5 µg/mL CD30 | 18690 | Not determined |
| HH 1 µg/mL CD30 | 19920 | Not determined |
| HH 0.2 µg/mL CD30 | 18403 | Not determined |
| U251 | 15 | Not determined |
| Colo-205 | <12 | Not determined |
| T cells with no target | <12 | 143 |
| T cells with 5 µg/mL CD30 and no target | 278 | 123 |

Table H shows that the addition of high concentrations of soluble CD30 protein to cultures containing target cells and 5F11-28Z-expressing T cells did not block the ability of the CAR T cells to recognize the CD30+ target cells. Previous estimates of the concentration of CD30 protein in serum and within lymphoma masses guided the choice of concentration of CD30 protein to add to the cultures of Table H (Nagata et al., *PNAS*, 102(22): 7946-7951 (2005)). Further evidence that anti-CD30 CARs can be effective at eradicating tumors despite the presence of soluble CD30 is provided by the murine experiments of Example 10. CD30 was detected by ELISA in the serum of 4 HH tumor-bearing mice at a mean concentration of 77 Units/mL, which corresponds to approximately 11 ng/mL. Despite this shedding of CD30 by HH cells, HH tumors were eradicated in mice as shown in FIG. 7A.

Example 12

This example demonstrates a dose-titration of cells transduced with 5F11-CD28Z.

Immunocompromised NSG mice were engrafted with $4 \times 10^6$ HH cells in a manner to form a solid mass. Mice were then treated with a single infusion of $6 \times 10^6$ untransduced T cells or a single infusion of $0.67 \times 10^6$, $2 \times 10^6$, or $6 \times 10^6$ T cells transduced with 5F11-CD28Z. T cells expressing 5F11-CD28Z were able to eliminate tumors in mice that received an infusion of $2 \times 10^6$ or $6 \times 10^6$ anti-CD30 CART cells; however, untransduced T cells or an infusion of $0.67 \times 10^6$ anti-CD30 CART cells was not able to eliminate tumors. Mice receiving 5F11-CD28Z-expressing T cells did not exhibit any signs of CAR T-cell-mediated toxicity. The mice did not exhibit ruffled fur or decreased activity, and the mice died only when sacrificed at the end of the experiments or when sacrificed after large tumors developed.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A chimeric antigen receptor (CAR) having antigenic specificity for CD30, the CAR comprising:
   (a) an anti-CD30 antigen binding domain comprising the heavy chain complementarity determining region (CDR) 1 amino acid sequence of SEQ ID NO: 1, the heavy chain CDR2 amino acid sequence of SEQ ID NO: 2, the heavy chain CDR3 amino acid sequence of SEQ ID NO: 3, the light chain CDR1 amino acid sequence of SEQ ID NO: 4, the light chain CDR2 amino acid sequence of SEQ ID NO: 5, and the light chain CDR3 amino acid sequence of SEQ ID NO: 6; and either (b) or (c):
   (b) (i) a hinge domain, a transmembrane domain, and an intracellular T cell signaling domain of human CD28 and (ii) an intracellular T cell signaling domain of human CD3ζ; or
   (c) (i) a hinge domain and a transmembrane domain of human CD8α; (ii) an intracellular T cell signaling domain of human CD28; and (iii) an intracellular T cell signaling domain of human CD3ζ.

2. The CAR of claim 1, wherein the antigen binding domain comprises the amino acid sequences of both of SEQ ID NOs: 7 and 8.

3. The CAR according to claim 1, wherein the hinge domain and the transmembrane domain of human CD8α comprise the amino acid sequence of SEQ ID NO: 11.

4. The CAR according to claim 1, wherein the intracellular T cell signaling domain of human CD28 comprises the amino acid sequence of SEQ ID NO: 12 and the intracellular T cell signaling domain of human CD3ζ comprises the amino acid sequence of SEQ ID NO: 15.

5. The CAR according to claim 1 comprising the amino acid sequence of SEQ ID NO: 17.

6. The CAR of claim 1, wherein the hinge domain, the transmembrane domain, and the intracellular T cell signaling domain of human CD28 comprises the amino acid sequence of SEQ ID NO: 13.

7. The CAR of claim 1, wherein the intracellular T cell signaling domain of human CD3ζ comprises the amino acid sequence of SEQ ID NO: 15.

8. The CAR of claim 1 comprising the amino acid sequence of SEQ ID NO: 16.

9. A nucleic acid comprising a nucleotide sequence encoding the CAR of claim 1.

10. A recombinant expression vector comprising the nucleic acid of claim 9.

11. A host cell comprising the recombinant expression vector of claim 10.

12. A population of host cells comprising at least two host cells of claim 11.

13. A pharmaceutical composition comprising the CAR according to claim 1 and a pharmaceutically acceptable carrier.

14. A method of treating cancer in a mammal, the method comprising administering to the mammal one or more host cells expressing the CAR of claim 1 in an amount effective to treat the cancer in the mammal, wherein the one or more host cell(s) is/are natural killer (NK) cell(s) or T cell(s).

15. The method of claim 14, wherein the cancer is lymphoma.

16. The method of claim 14, wherein the one or more host cells is/are autologous to the mammal.

17. The method of claim 14, wherein the one or more host cells is/are allogeneic to the mammal.

18. A pharmaceutical composition comprising the population of host cells according to claim 12 and a pharmaceutically acceptable carrier.

19. The CAR of claim 1 encoded by a nucleotide sequence encoding the following components from the 5' to the 3' end: (i) the antigen binding domain, (ii) the hinge domain, the transmembrane domain, and the intracellular T cell signaling domain of human CD28 and (iii) the intracellular T cell signaling domain of human CD3ζ.

20. The CAR of claim 1 encoded by a nucleotide sequence encoding the following components from the 5' to the 3' end: (i) the antigen binding domain, (ii) the hinge domain and the transmembrane domain of human CD8α; (iii) the intracellular T cell signaling domain of human CD28; and (iv) the intracellular T cell signaling domain of human CD3ζ.

21. The CAR of claim 1 comprising intracellular T cell signaling domains of no more than human CD28 and human CD3ζ.

* * * * *